(12) United States Patent
Von Schuckmann

(10) Patent No.: US 6,722,363 B1
(45) Date of Patent: Apr. 20, 2004

(54) DEVICE FOR EMPTYING CAVITIES CONTAINING POWDER BY MEANS OF SUCTION

(75) Inventor: Alfred Von Schuckmann, Kevelaer (DE)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 09/719,786

(22) PCT Filed: Jun. 22, 1999

(86) PCT No.: PCT/EP99/04304

§ 371 (c)(1),
(2), (4) Date: May 23, 2001

(87) PCT Pub. No.: WO99/66974

PCT Pub. Date: Dec. 29, 1999

(30) Foreign Application Priority Data

| Jun. 22, 1998 | (DE) | 198 27 731 |
| Jul. 9, 1998 | (DE) | 198 30 713 |
| Aug. 29, 1998 | (DE) | 198 39 516 |
| Dec. 4, 1998 | (DE) | 198 55 851 |

(51) Int. Cl.[7] .............................................. B65D 83/06
(52) U.S. Cl. .......................... 128/203.15; 128/203.21; 128/203.23; 604/58; 141/329
(58) Field of Search ................. 128/203.15, 203.18, 128/203.21, 203.23, 203.24; 604/57, 58, 87; 141/329, 330

(56) References Cited

U.S. PATENT DOCUMENTS 2,549,303 A 4/1951 Friden

| 5,415,162 A | 5/1995 | Casper et al. |
| 5,435,301 A | 7/1995 | Herold et al. ........... 128/203.15 |
| 5,647,349 A * | 7/1997 | Ohki et al. ............ 128/203.15 |
| 5,785,049 A * | 7/1998 | Smith et al. ........... 128/203.15 |

FOREIGN PATENT DOCUMENTS

| DE | 196 19 536.5 | 5/1996 |
| EP | 843 03 490.1 | 5/1984 |
| EP | 0129985 | 1/1985 |
| EP | 911 11 238.1 | 7/1991 |
| EP | 0467172 | 1/1992 |
| HU | 213495 B | 7/1997 |
| HU | 213661 B | 9/1997 |
| HU | 216509 B | 7/1999 |
| WO | WO 92/04068 | 3/1992 |
| WO | WO 94/12142 | 6/1994 |

OTHER PUBLICATIONS

Copy of Search Report.

* cited by examiner

Primary Examiner—Timothy L. Maust
(74) Attorney, Agent, or Firm—Fish & Richardson P.C.

(57) ABSTRACT

The invention relates to a device (V) for emptying powder-containing cavities (1) sealed by means of a covering foil (9) by means of a suction tube (11) which can be set by hand and whose leading end is positioned relatively to the cavity (1) and pierces in a guided manner the covering foil (9), leaving a free cross section for air to flow into the cavity (1), and, to achieve a solution which is beneficial for production and reliable in manipulation, proposes that the leading end of the suction tube (11) has, adjacent and axially projecting with respect to cutting edges (12) provided at that point, extensions (22/82) which are guided in slots (19 and/or 83, 55 or 25, respectively) of a carrier (T) adjacent to the cavities (1) in a shape-locked/rotationally fixed manner, in which carrier (T) the cavities (1) can be inserted as blister packs (2).

65 Claims, 28 Drawing Sheets

Figure 7:
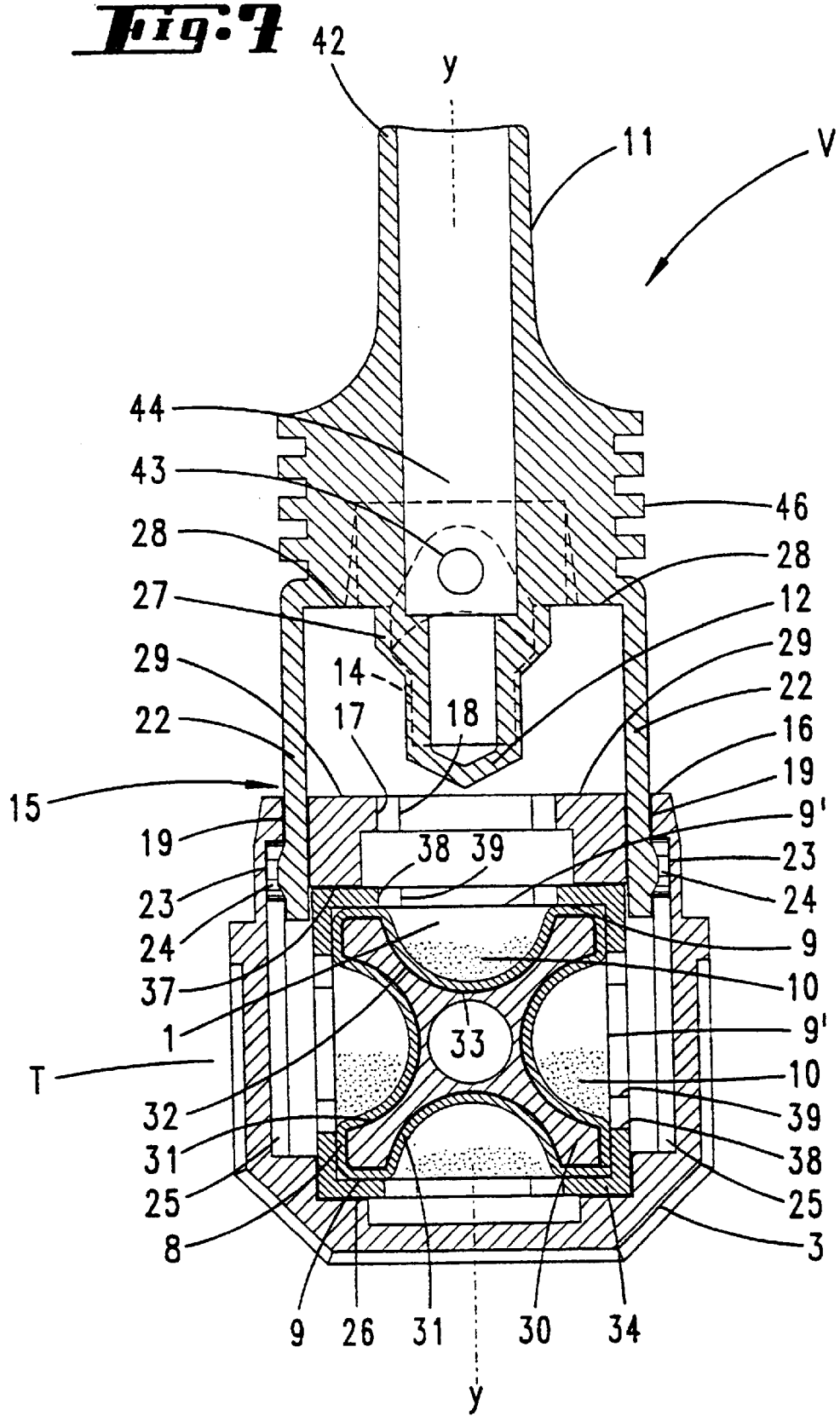

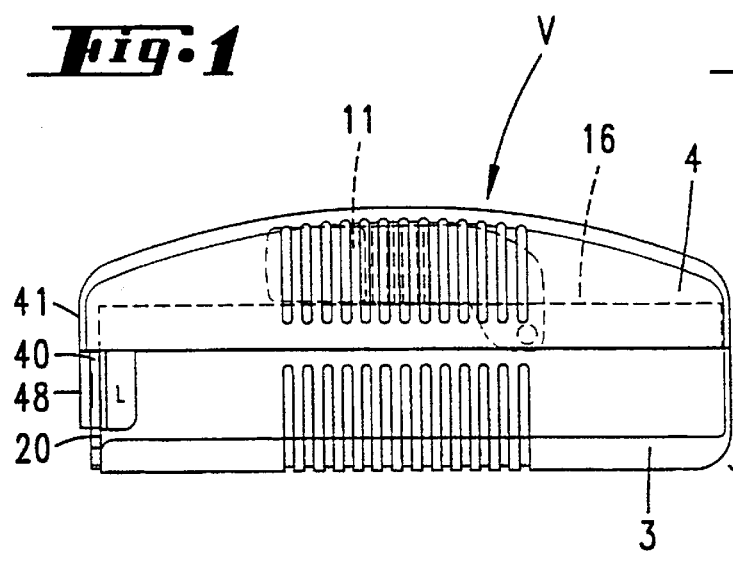
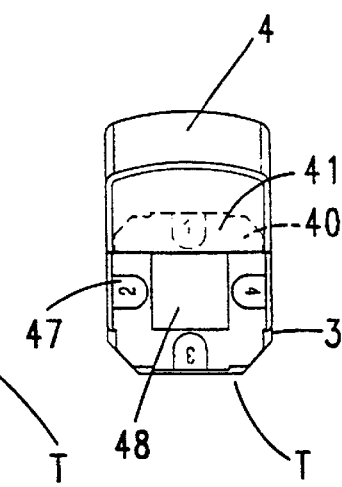
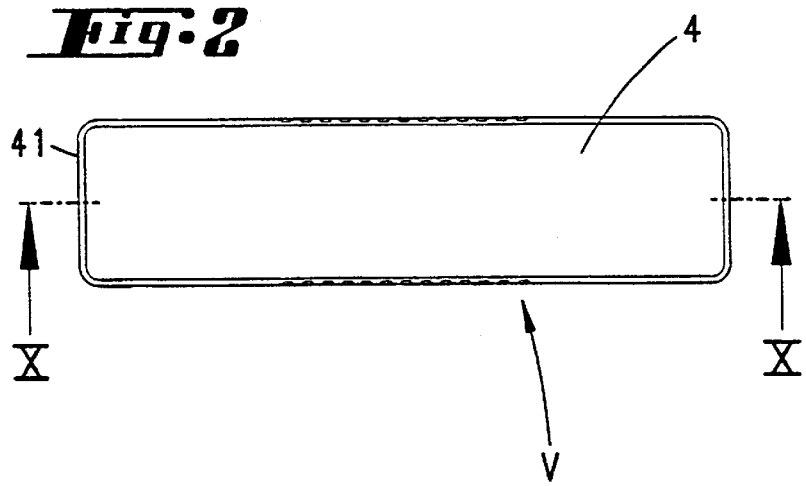

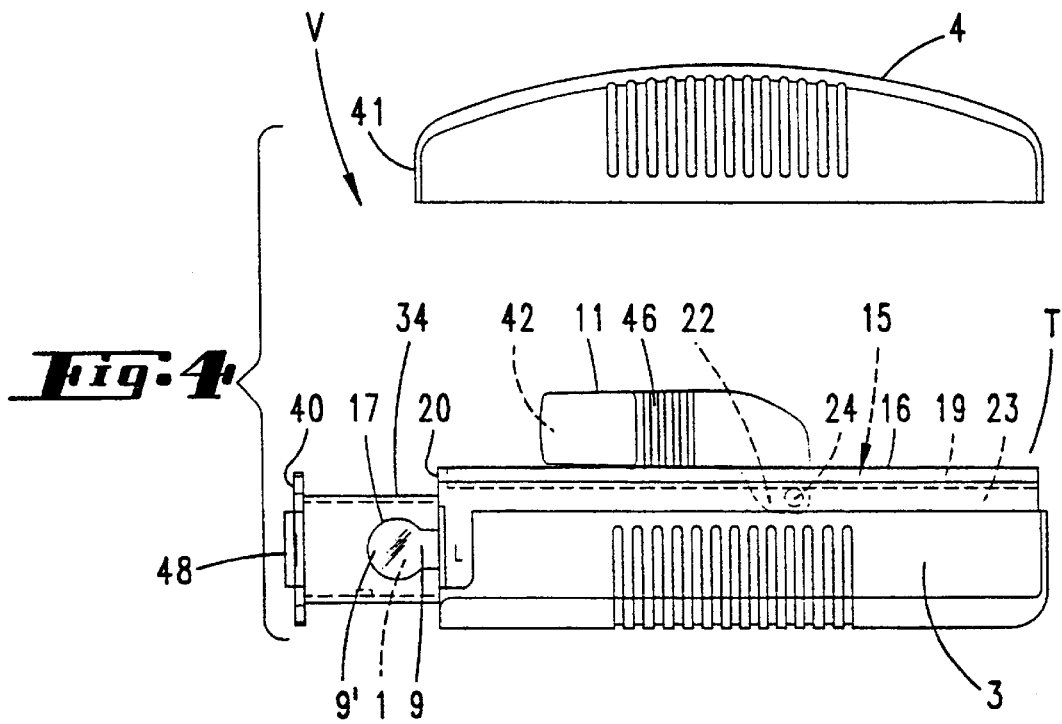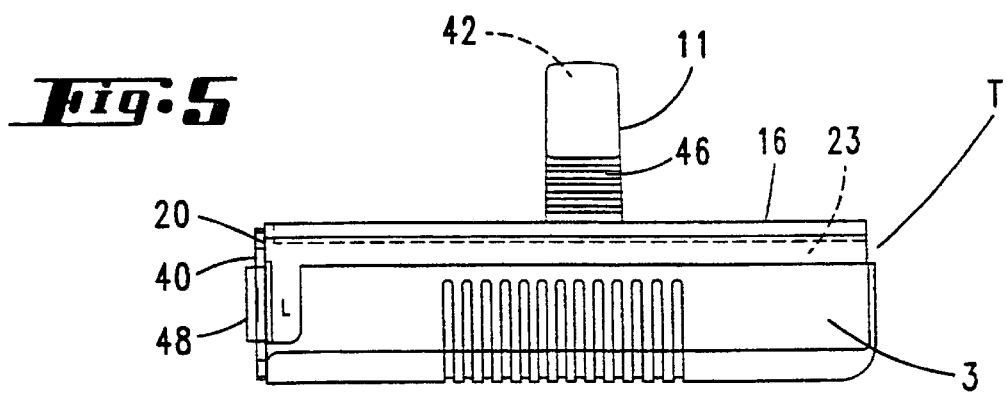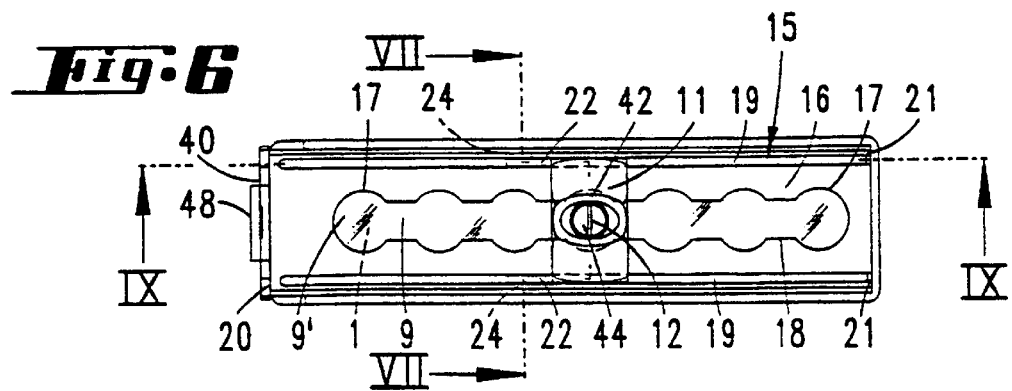

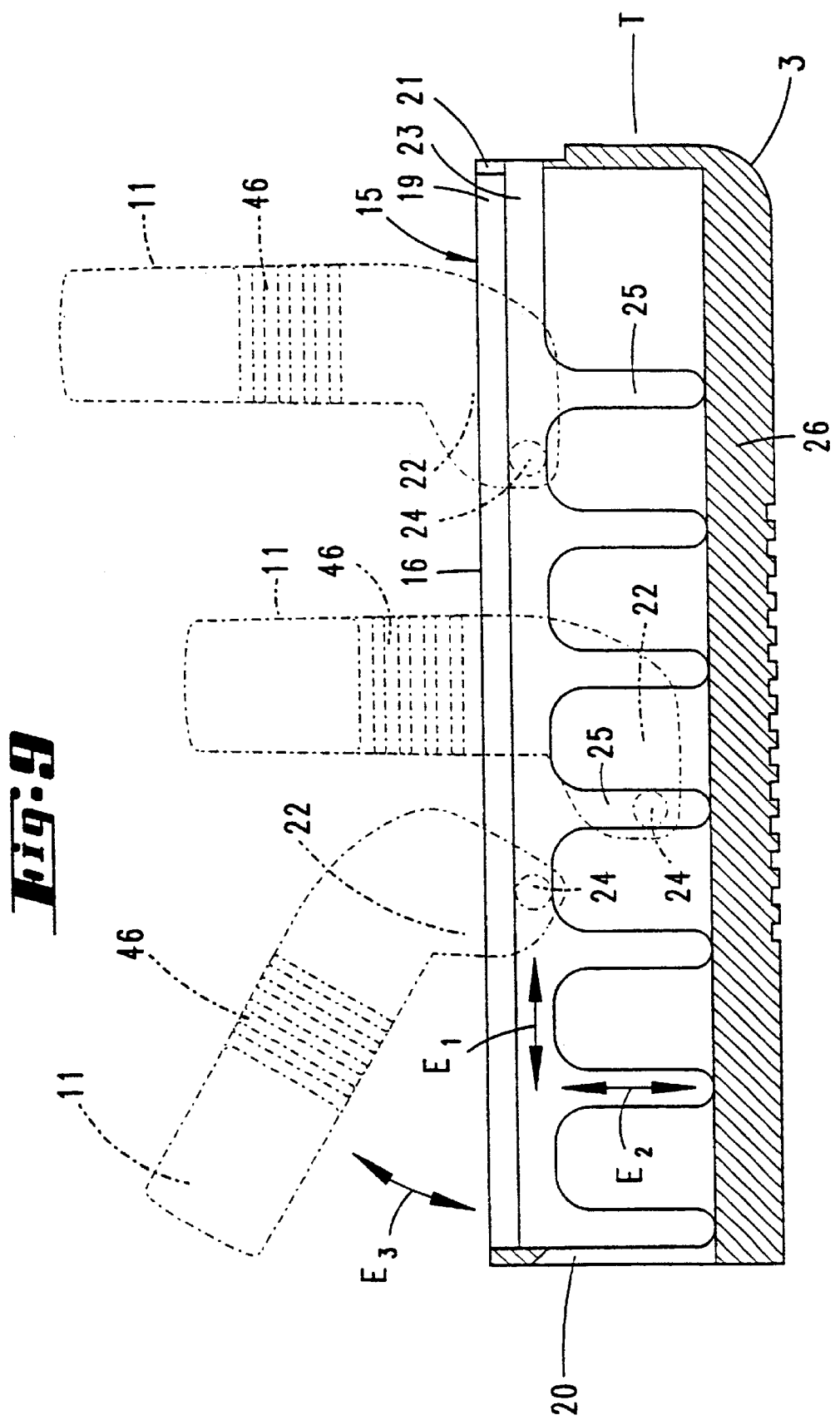

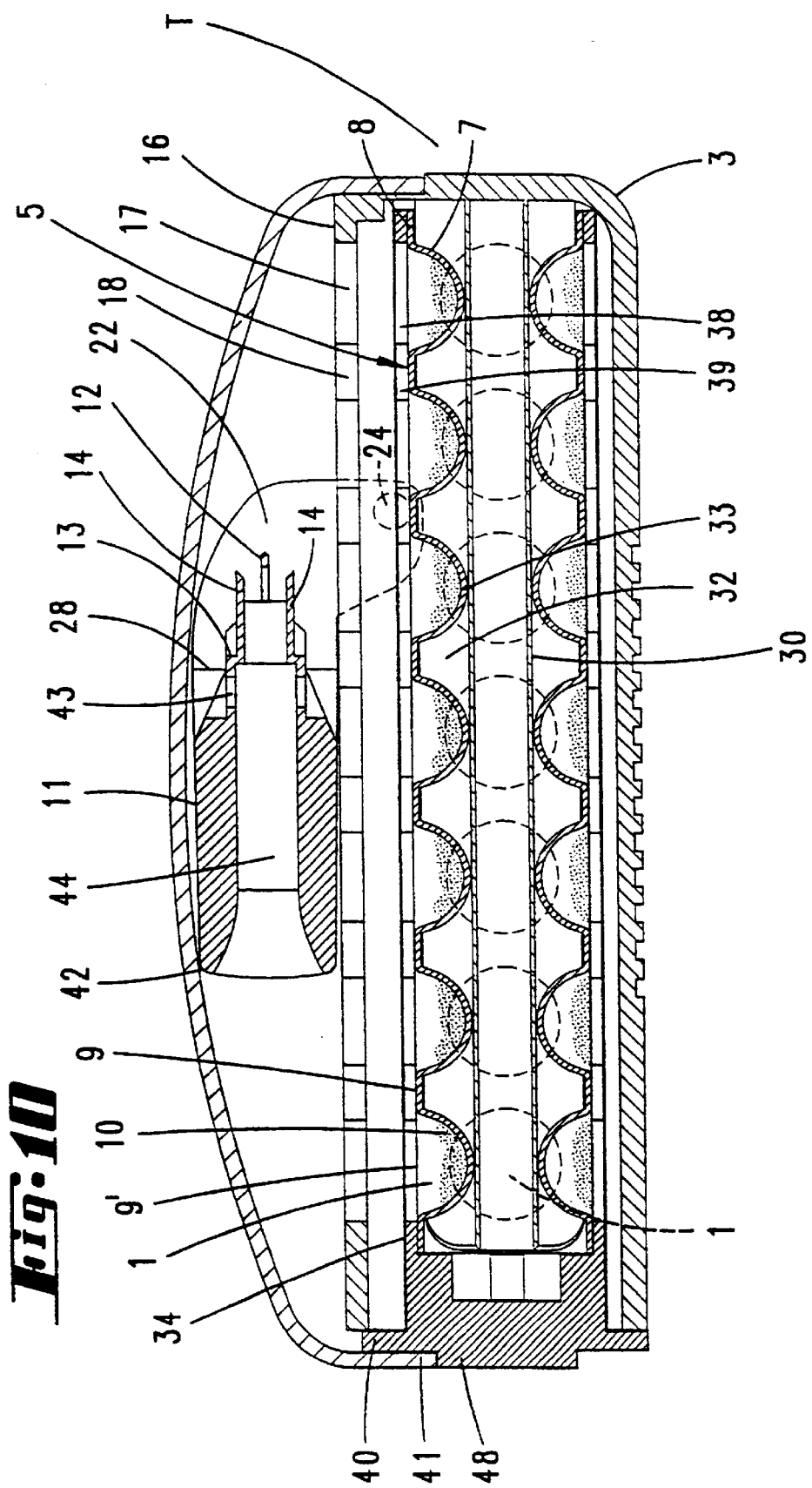

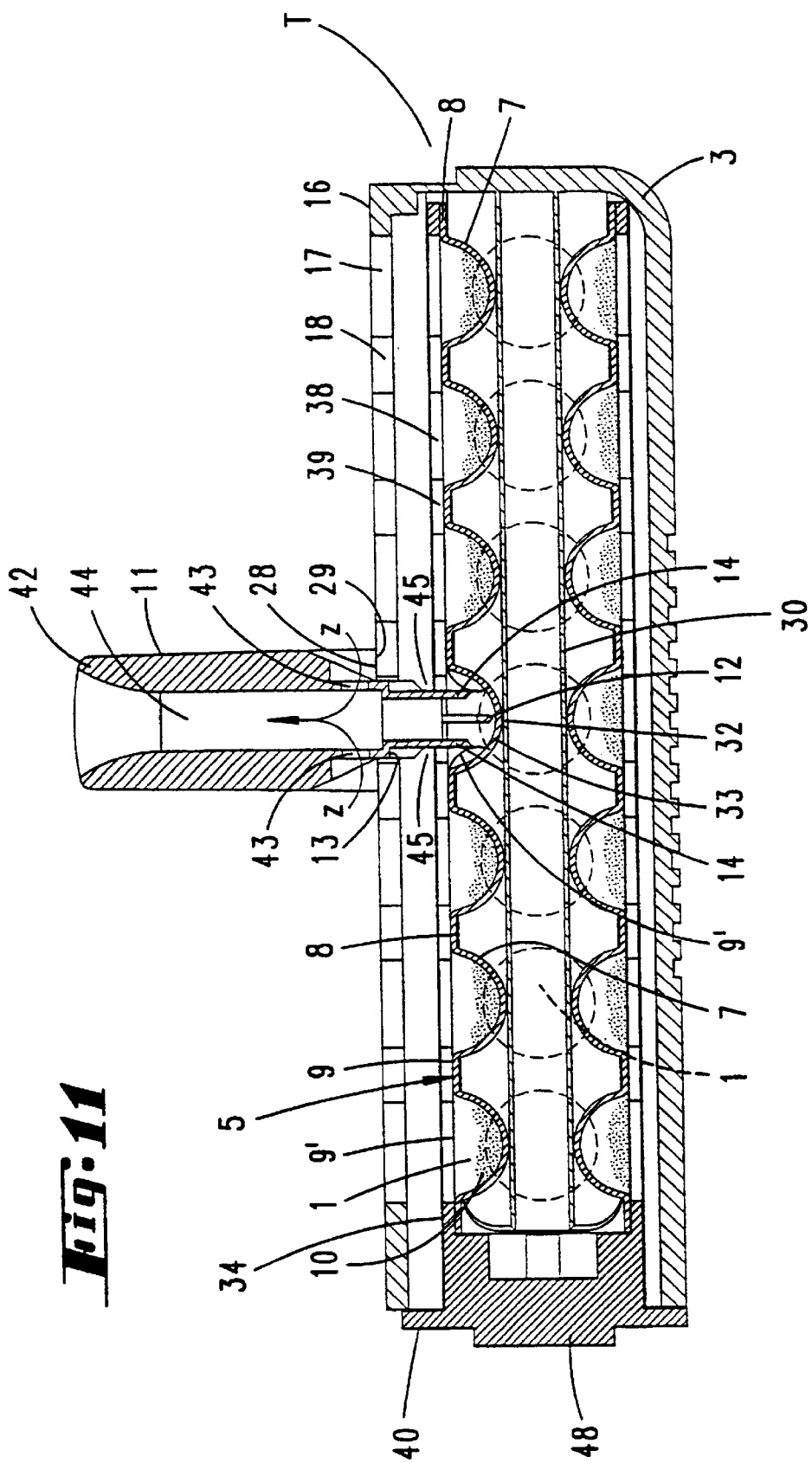

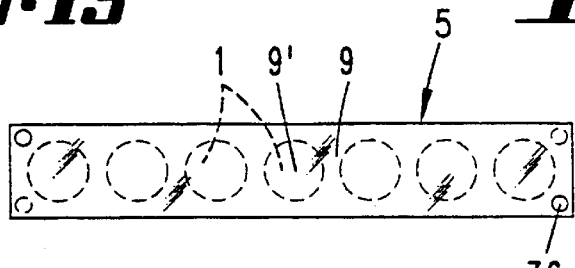
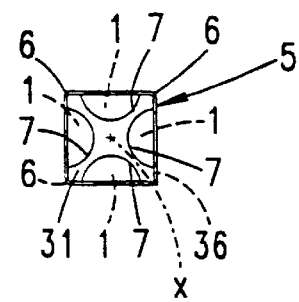
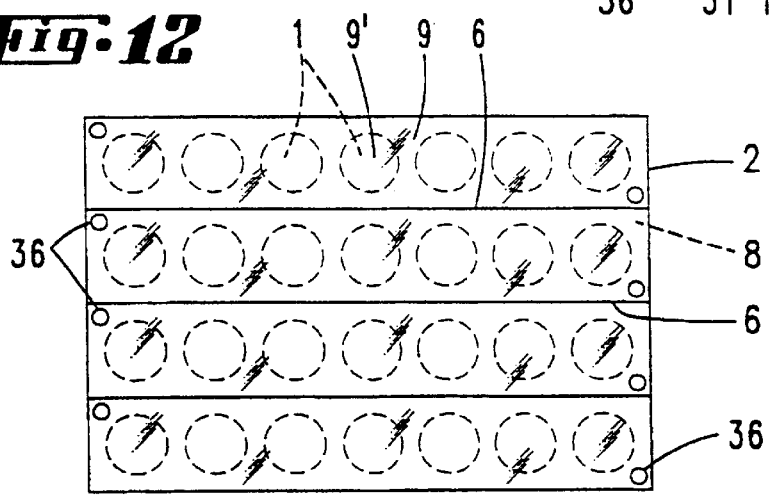
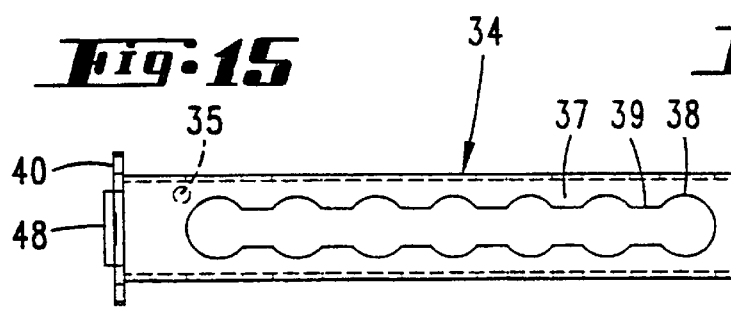
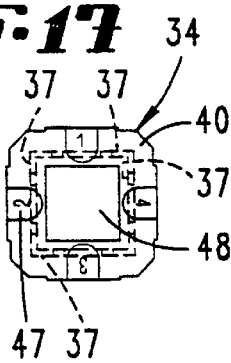
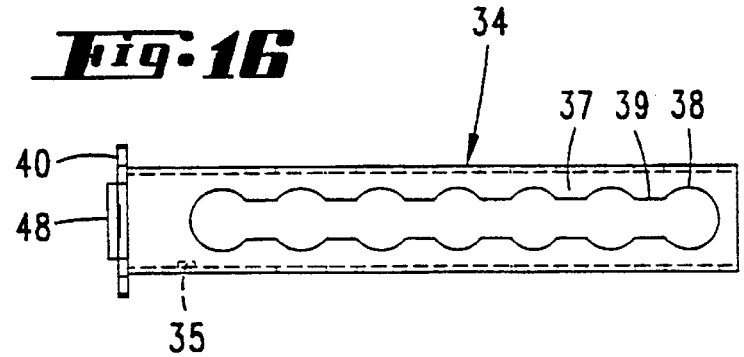

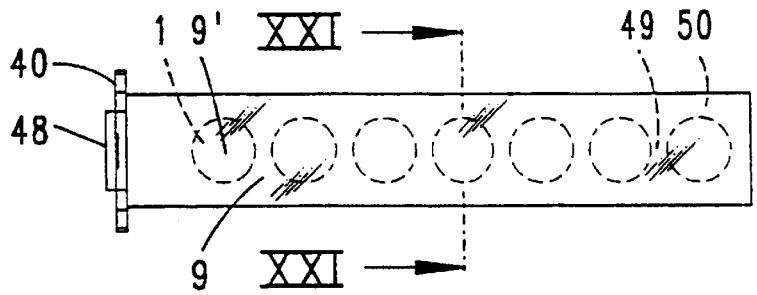
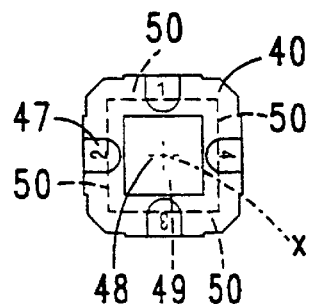
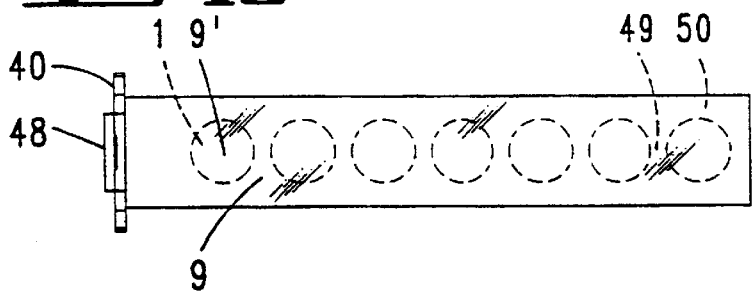
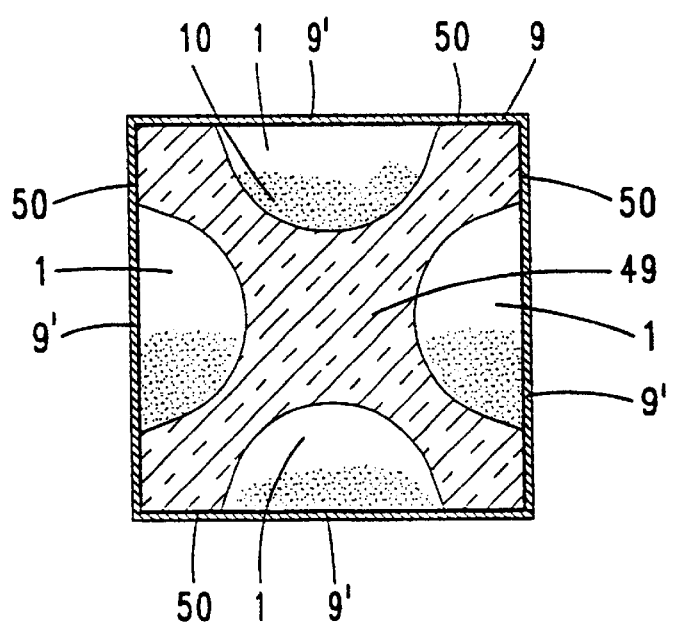

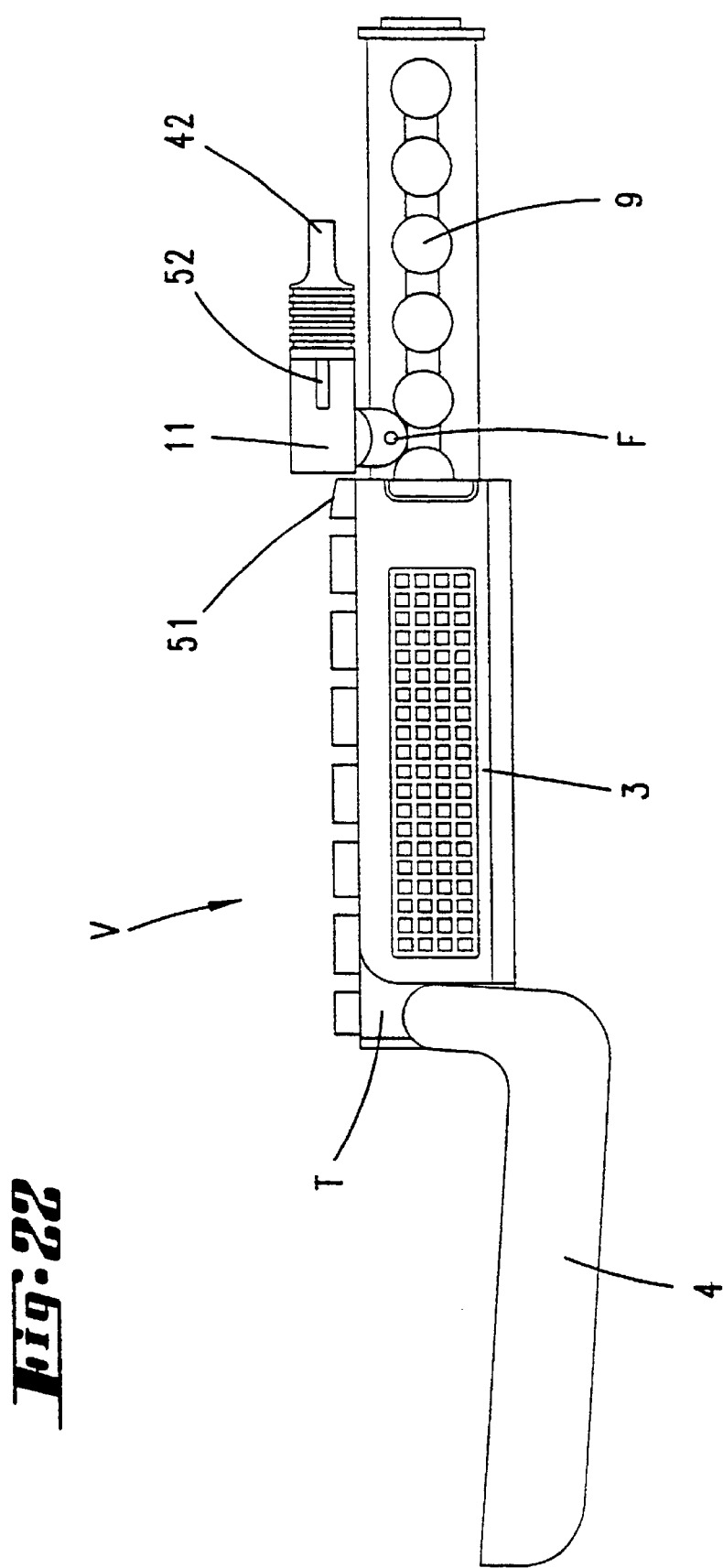

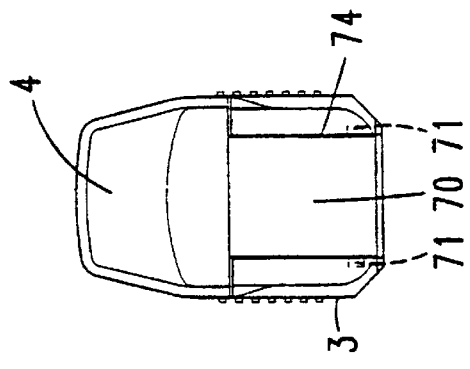
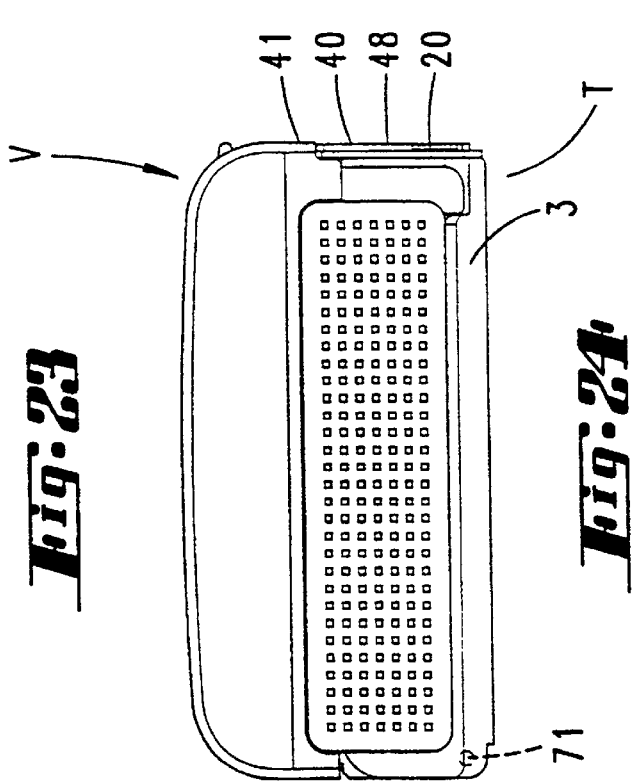
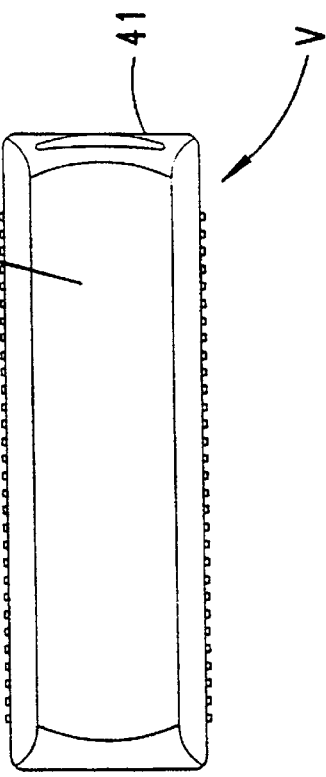
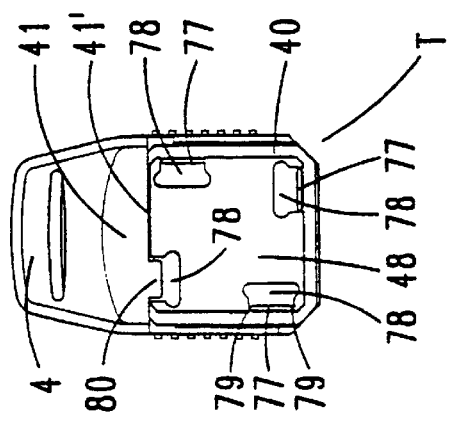

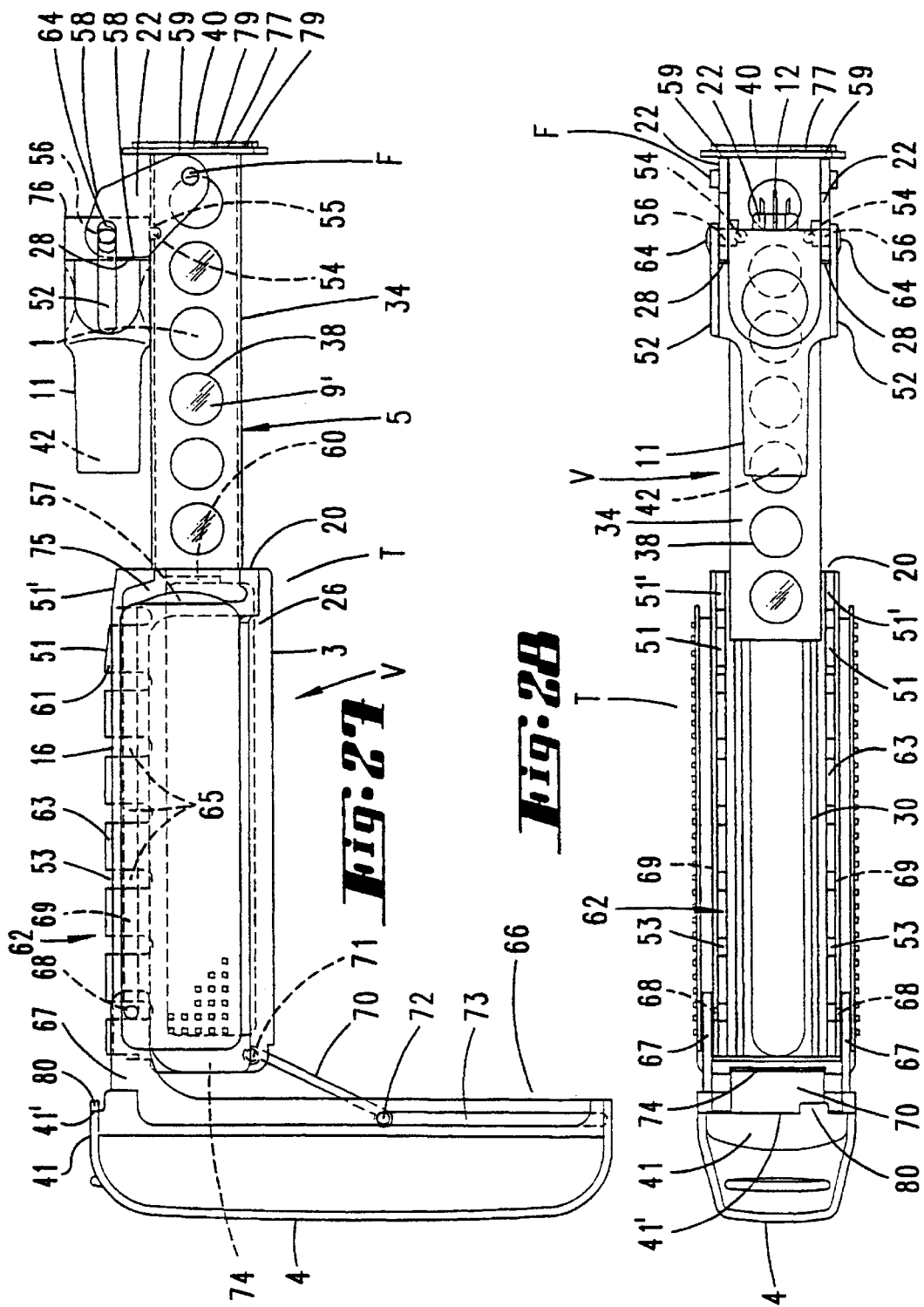

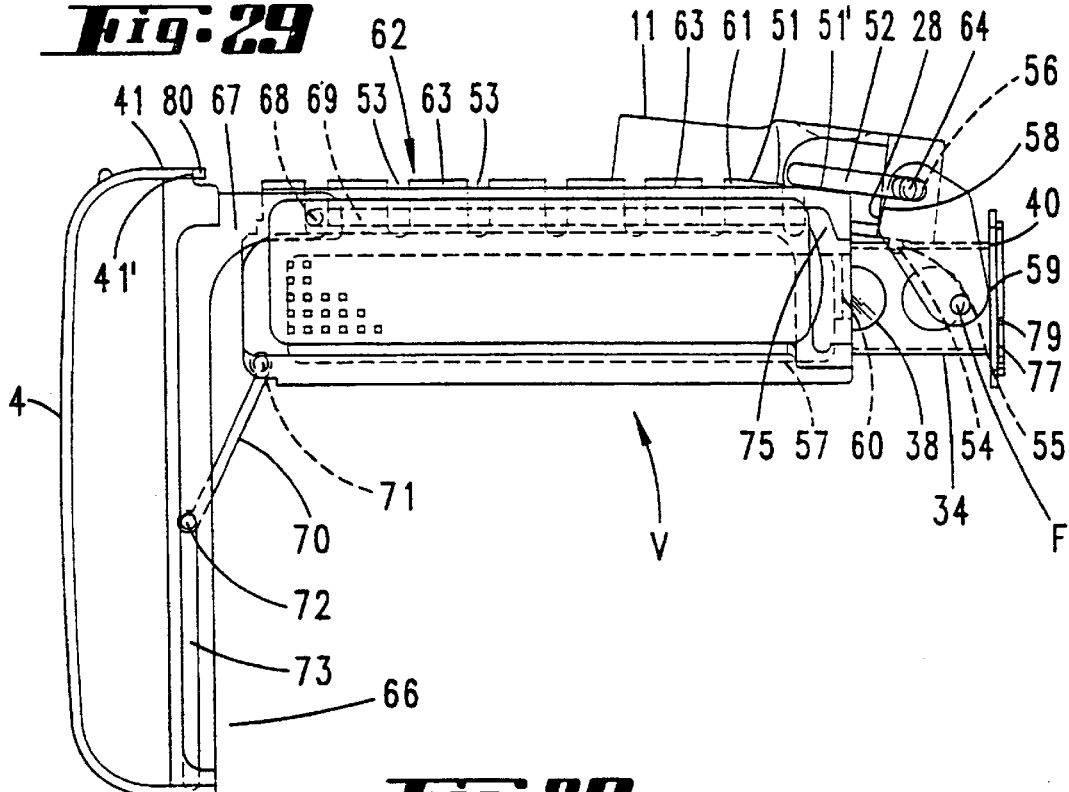
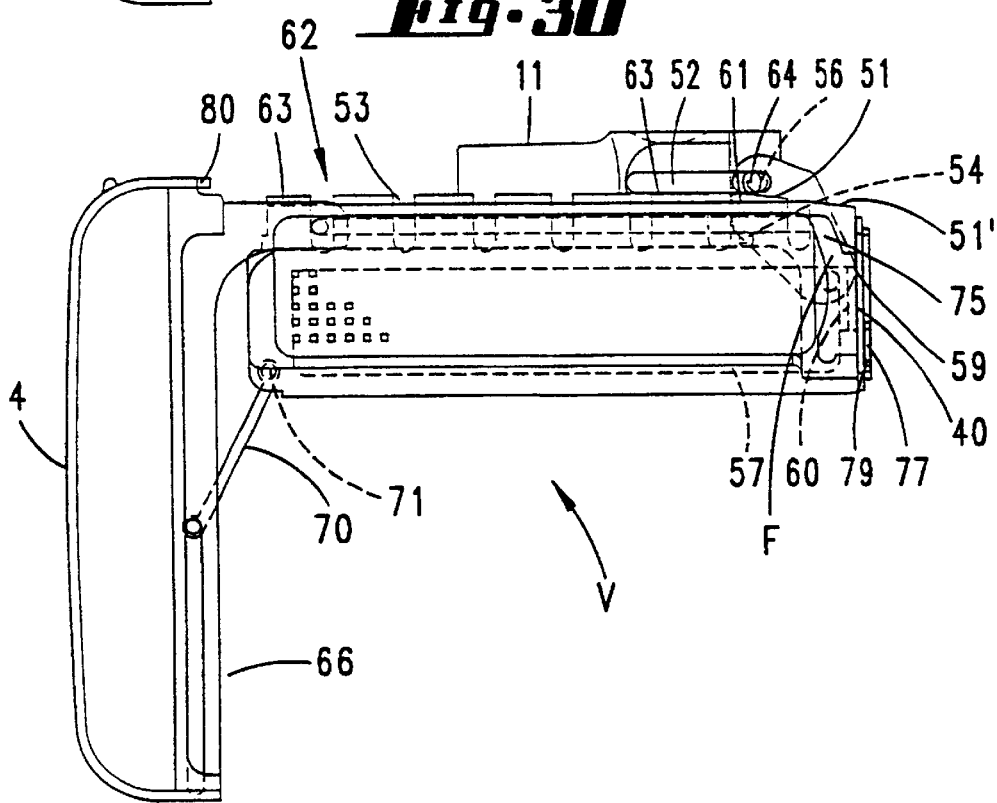

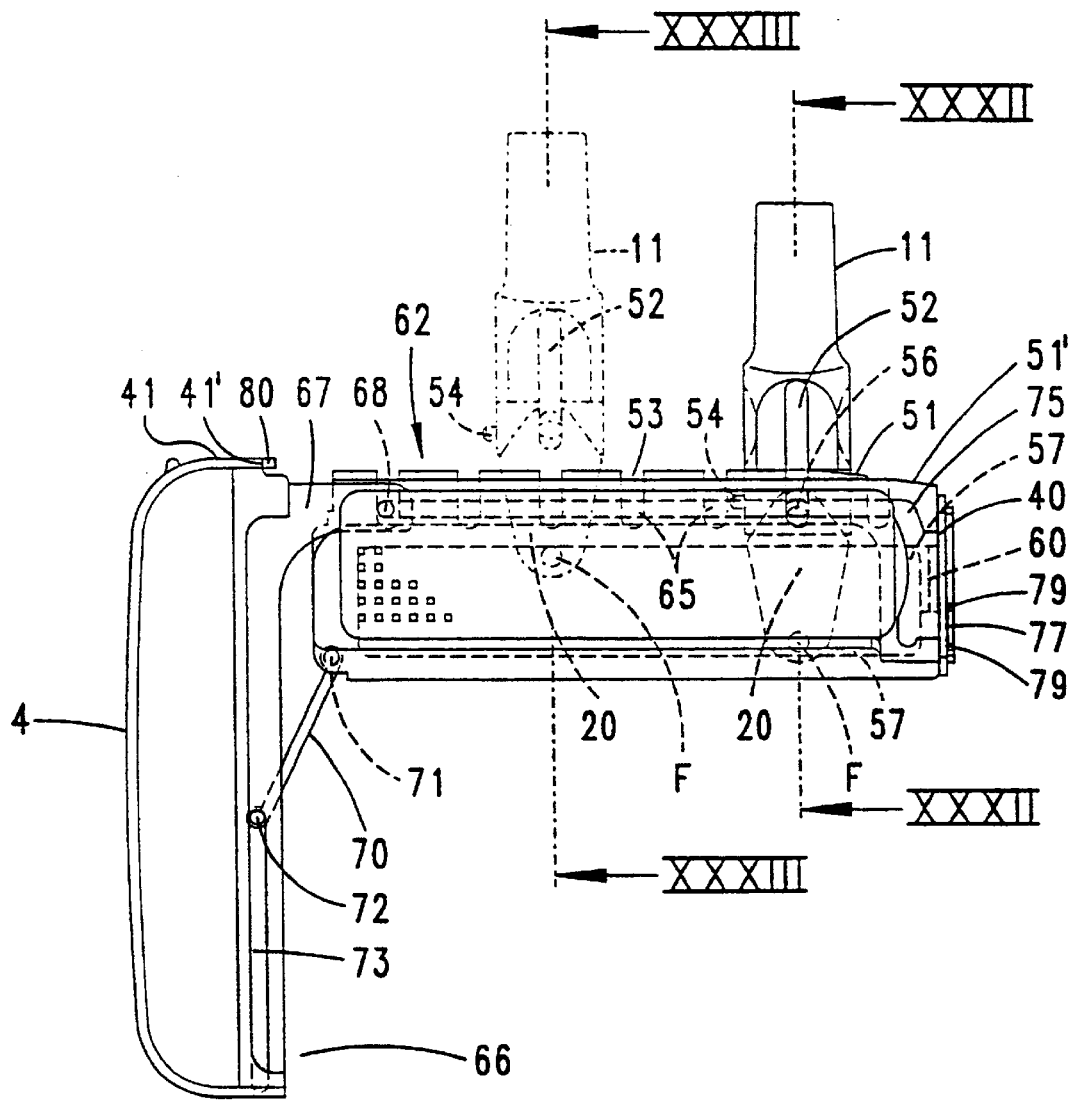

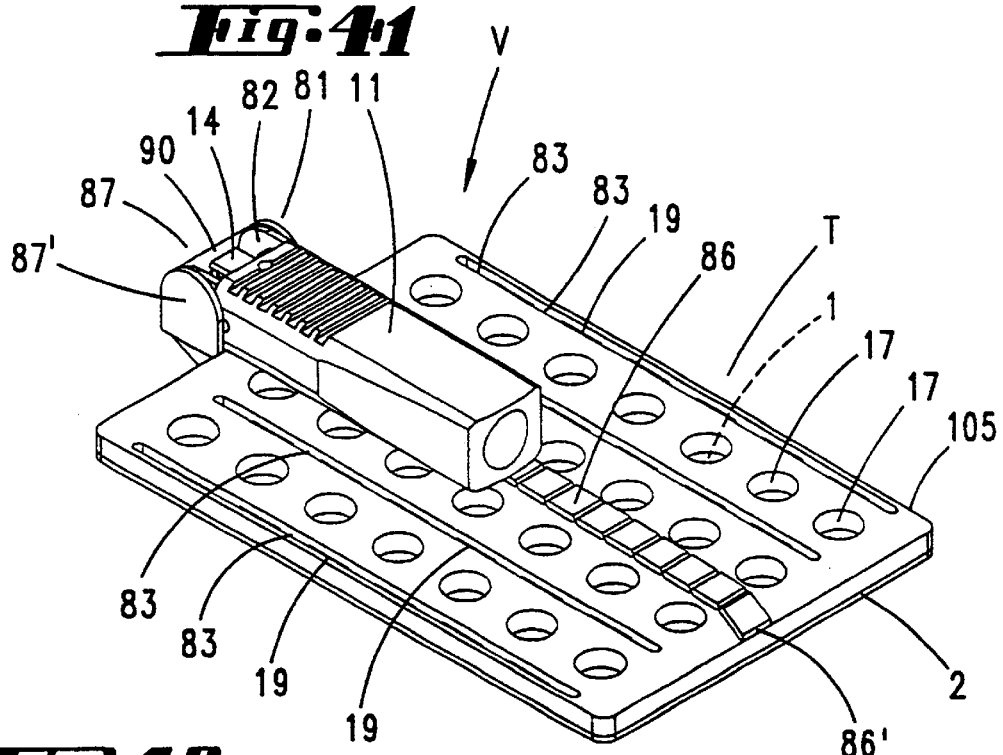
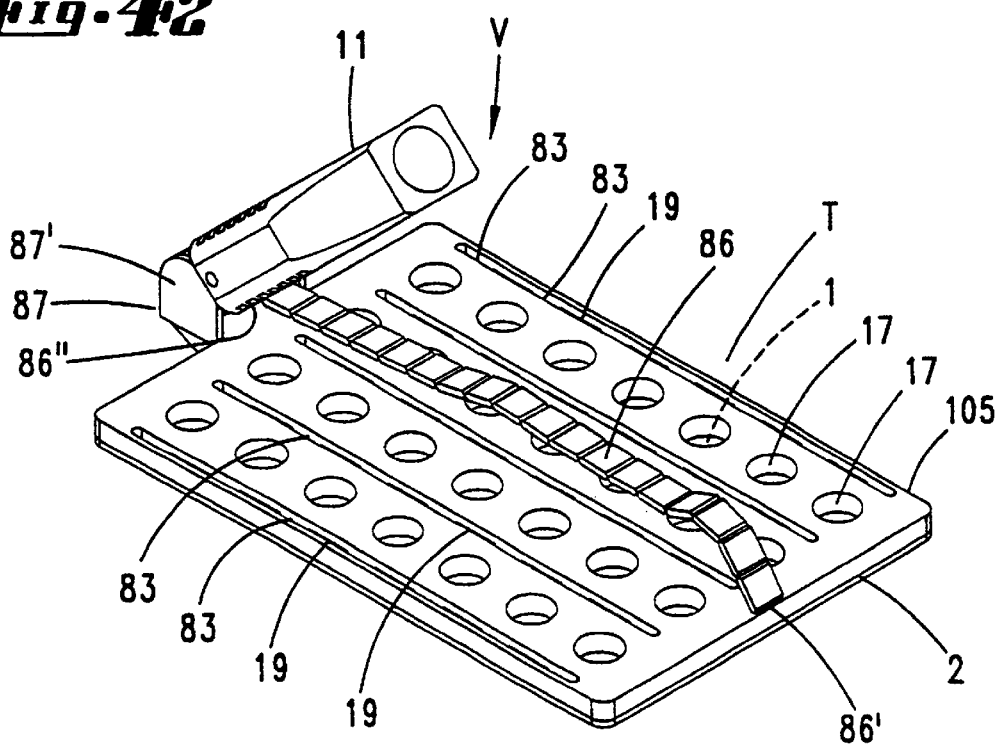

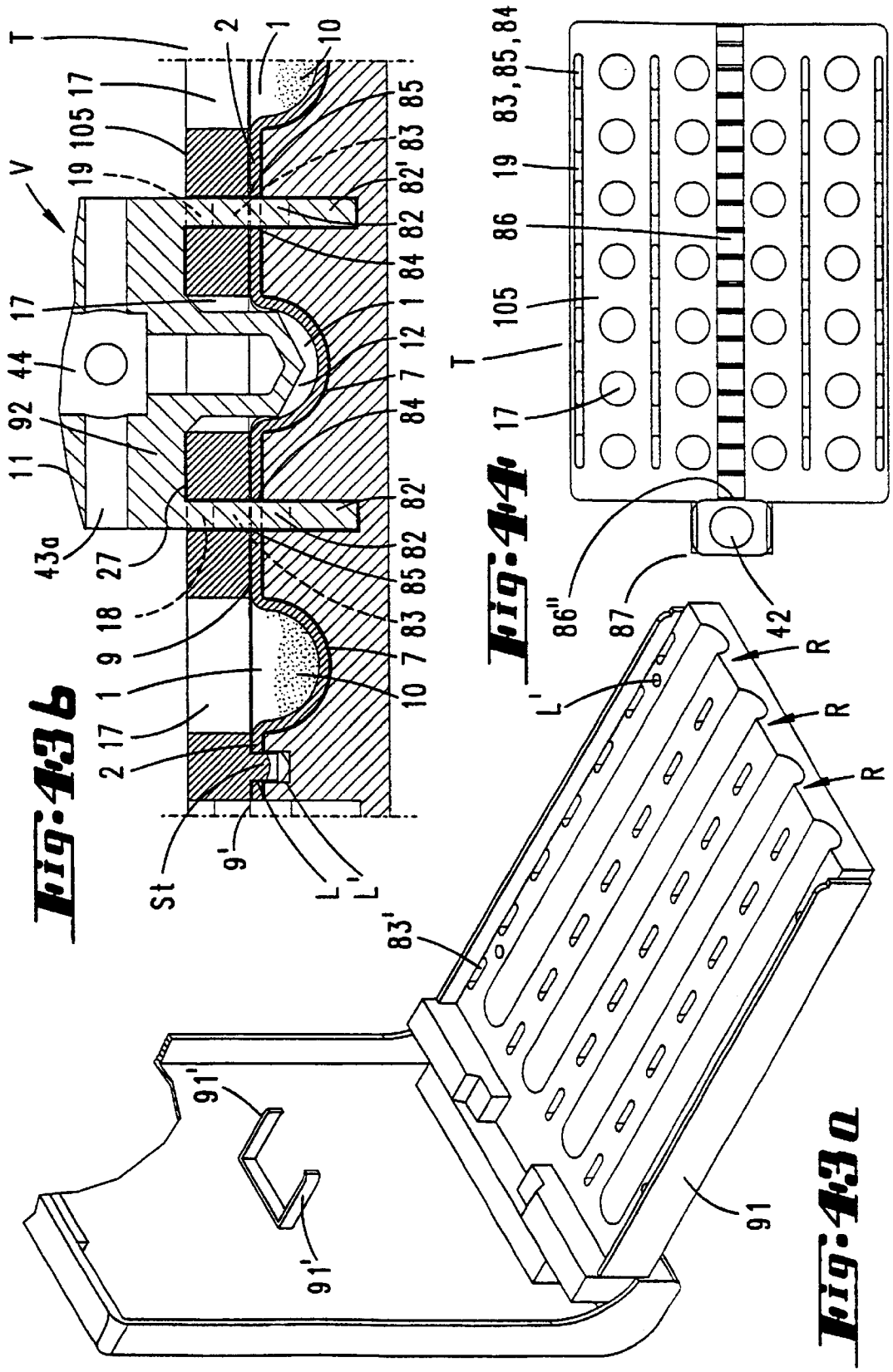

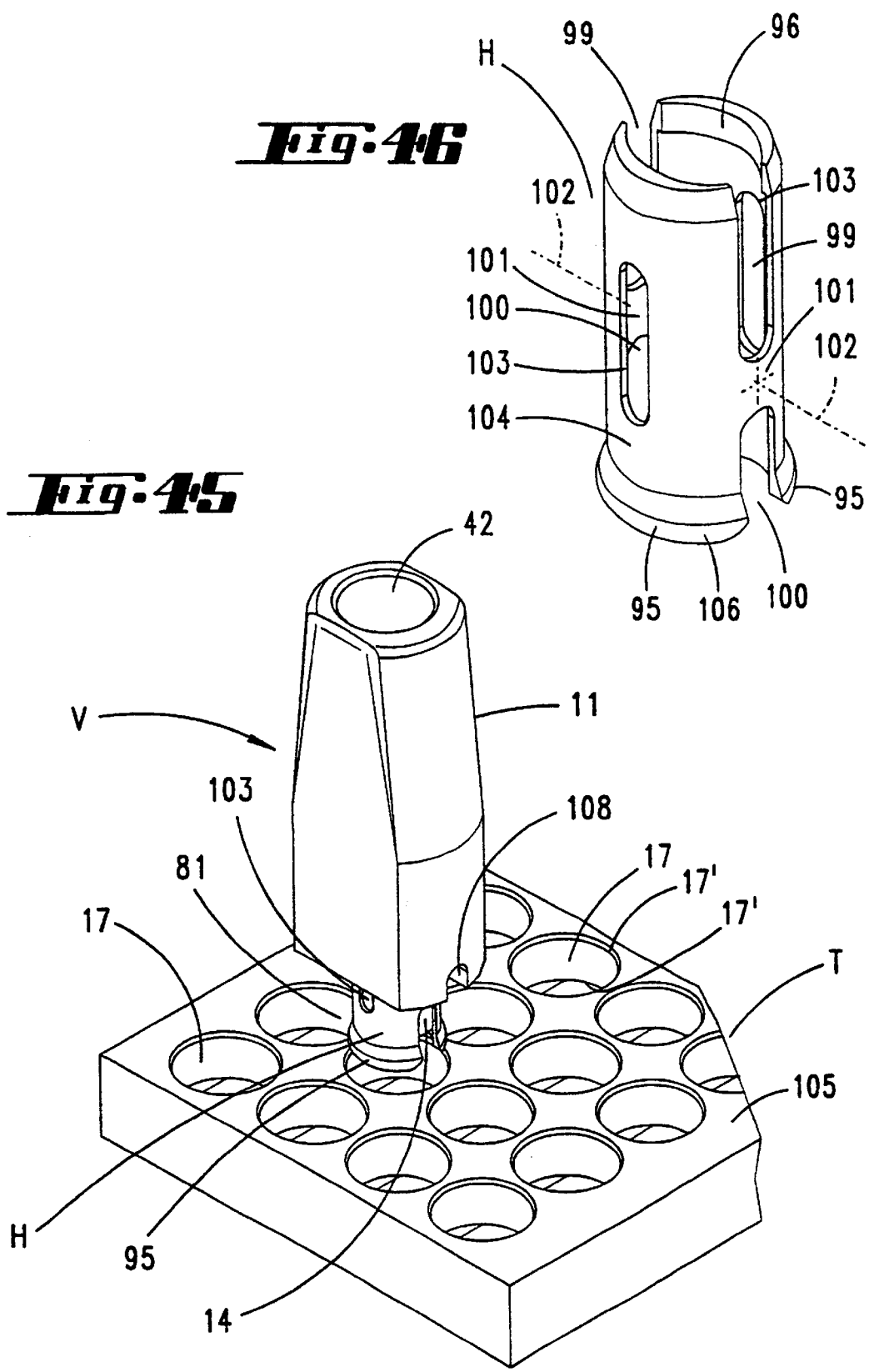

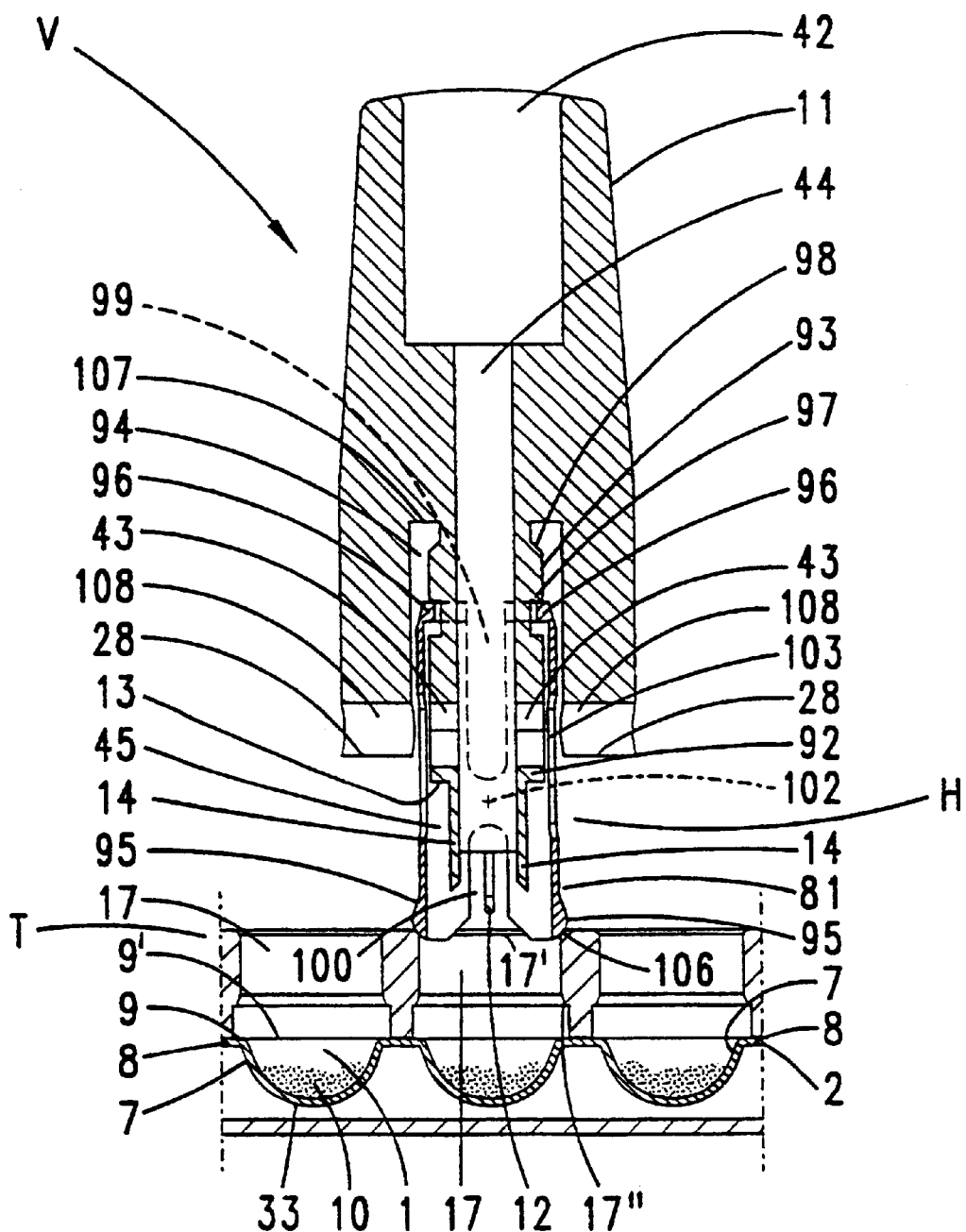

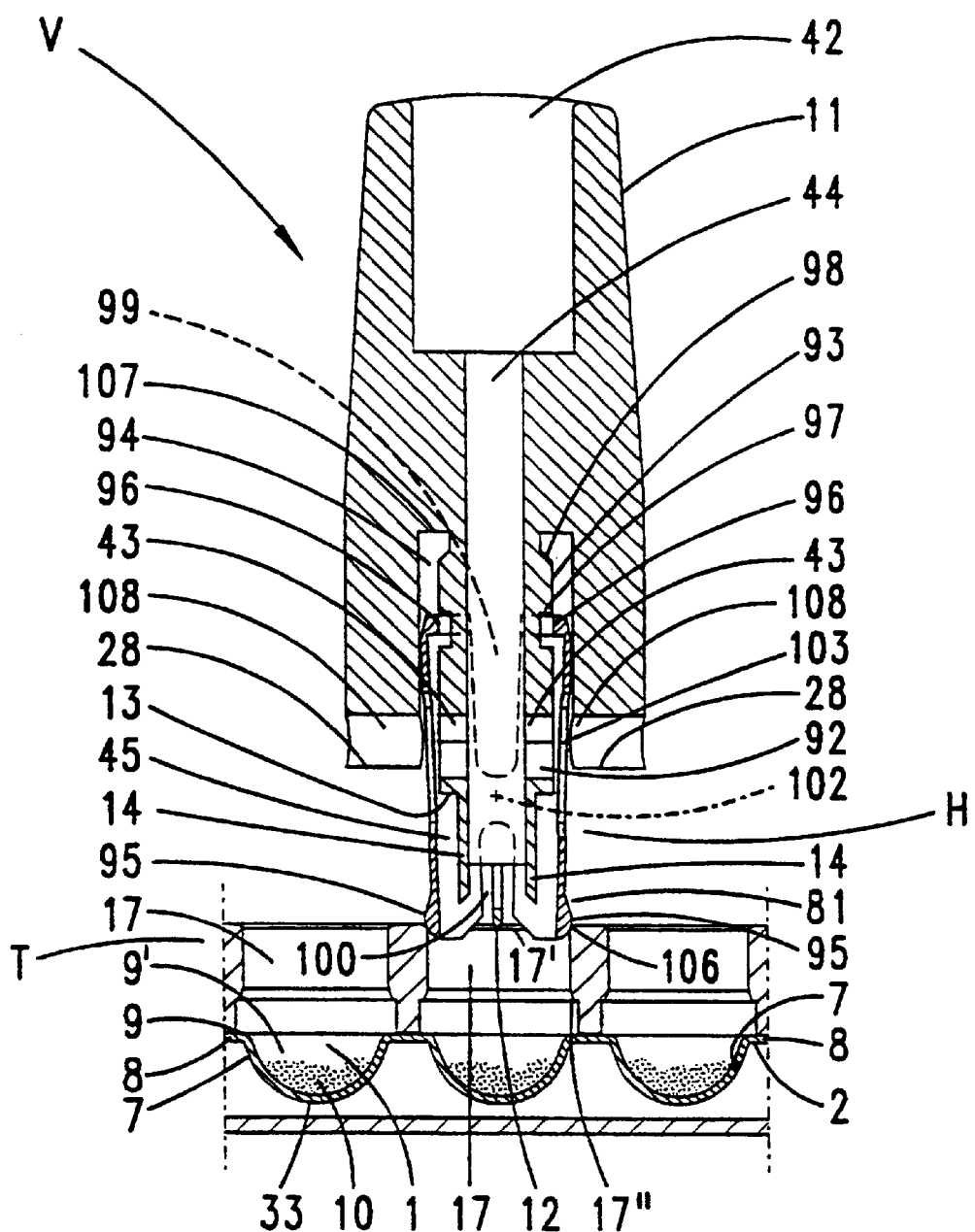

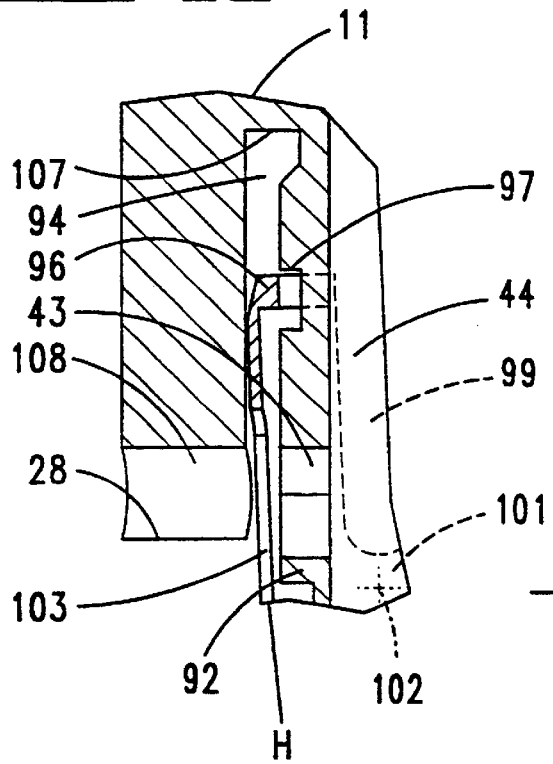
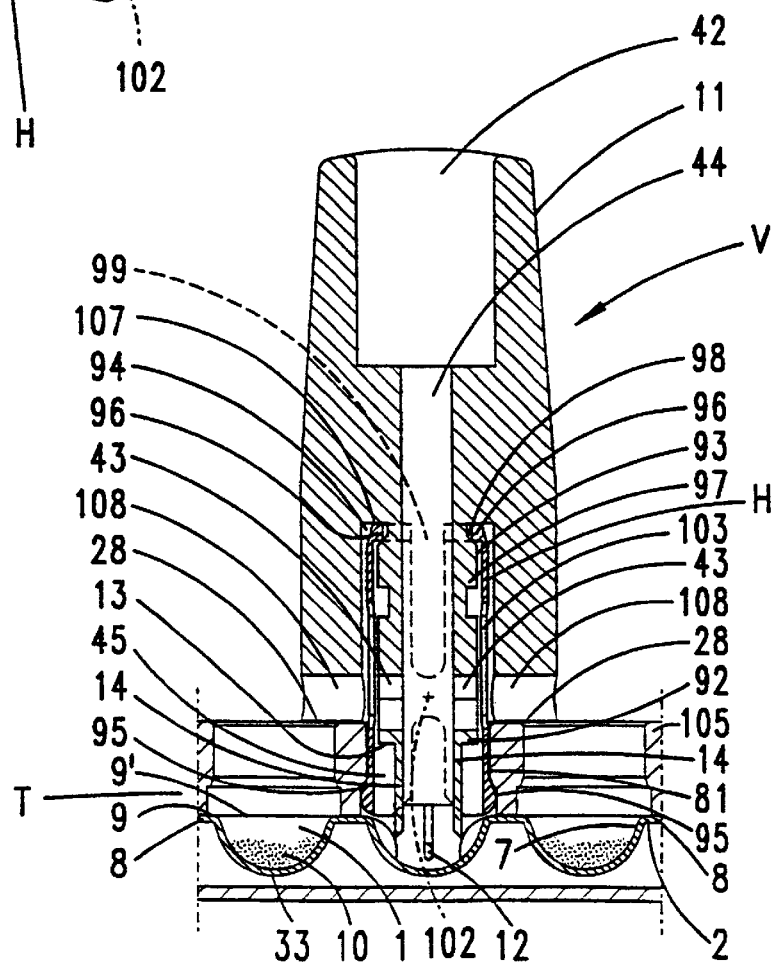

DEVICE FOR EMPTYING CAVITIES CONTAINING POWDER BY MEANS OF SUCTION

The invention relates to a device for emptying powder-containing cavities by suction in accordance with the generic concept of claim 1 or 53.

In the prior published solutions of this type (US-PS 25 49 303), the cavity is provided in a solid lower part which has a pot-shaped recess over whose pot rim the covering foil is stretched. The suction tube is fitted at its leading end with an annular collar which can be pushed in lid fashion onto the outer surface wall. Provided in the upper part in a re-entrant manner with respect to said rim is a truncated cone whose leading, narrower truncated-cone end face pierces the covering foil when the suction tube is pressed down. A channel-shaped cross-section is left in the inner surface of the encircling wall of the annular collar for the entrance of air while the cavity is being emptied by suction. The solutions are inadequate structurally and operationally: the outer enclosure leaving only a small air entrance cross section makes it impossible always to achieve a uniform, in particular complete, emptying of the cavity. This also contributes to the fact that the leading, cross-sectionally smaller truncated-cone end face does not make possible a controlled opening separation of the covering foil so that cases occur in which portions of the covering foil which have awkwardly folded into position propel residues of the powder to be sucked out into a concealed position which is also favoured by the fact that such cover-foil portions are possibly sucked onto the truncated-cone outer surface. The fact that the suction tube is rotatable relative to the lower part and may even be rotated further after the covering foil has been pierced during the manipulation adversely affects the reproducibility of the suction emptying process. That makes use in the field of medications which have to be precisely dispensed impossible. In addition, the lower part, which forms the cup-shaped cavity, is conceived as a disposable part and is thrown away after the covering foil has been pierced, which is an appreciable cost-increasing factor, apart from the storing for the cases of a regular medicinal taking of the powder.

Another solution which avoids the last mentioned disadvantage is prior published by DE-OS 196 19 536. In the latter, a carrier is provided to which a standard blister pack can be fitted with a multiplicity of cavities which each contain the powder in the appropriate dosage. This has not only the advantage of reusability of the carrier as a result of filling with a new blister pack, but also the advantage that a plurality of cavities is always provided and, in the case of medicinal application, the patient also has a certain inspection ability in regard to the covering foil already pierced and to the cavities still unused. In this connection, the carrier has a cover plate which has individual holes which align with the cavities of the blister. The suction tube is first positioned in the latter and then brought right into the suction position by further insertion. In this arrangement, flanks are fitted to the suction tube which cut at the leading end and which ensure a specific separation of the respective covering foil of the cavity, which separation optimizes the emptying by suction. The necessary air entrance cross sections which permit the replacement flow of air into the cavities when the latter are emptied by suction are in this case designed as axial tubular channels of the suction tube whose leading mouth cross sections are exposed in the cavity after the covering foil has been pierced.

The respective solutions are disadvantageous in regard to the fact that the freely projecting blades are very susceptible to damage during the initial positioning of the suction tube in the hole of the carrier. In order to protect them against damage to any extent at all during the piercing of the covering foil, the suction tube has to be already longitudinally guided into the holes before the blade contacts the covering foil. That necessitates a relatively great axial length of said insertion holes of the carrier, which in turn has the disadvantage that the blister covering foil is situated quite far below the upper side of the carrier and it is consequently often possible to check only with difficulty whether a certain cavity has already been sucked empty or not. In the case of this prior published solution, if the insertion end of the suction tube is made non-circular, it is true that a rotation of the suction tube is prevented after mutual engagement of this non-circular region in the correspondingly non-circular hole of the carrier, and there will be damage, associated therewith, to the blade as a result of rotation of the latter in the cut covering foil; the solution in regard to the air entrance cross sections to form them as tubular channels of the suction tube, however, thereby, becomes even more complicated. As uniform as possible a suction of said air from all sides into the cavity, which actually does give as equal treatment as possible to all the regions of the cavity, is not achievable.

The object of the invention is to form a generic device in such a way that it can be produced more inexpensively and can be manipulated more reliably.

In the case of claim 1, this object is achieved in that the suction tube is positioned in slots of the carrier separated from the entrance hole for the blades or, in the case of the solution of claim 53, in that a sleeve positions itself at the rim of the hole of the carrier and then undertakes the guidance of the suction tube during the insertion movement, said separate positioning means being in both cases a protection of the cutting flanks against damage even when not in use, which cutting flanks can thereby be adapted in an optimum way to provide the advantage of cutting through the covering foil portion and of folding in the individual cut covering foil sectors.

As a result, there is actually also the advantage of a concentrated control of the device. The cover of the carrier, which cover is provided with holes and under which the blister is situated may be very thin; nevertheless, there is an adequate positioning of the suction tube, in good time before the blades pass into the hole. The blister covering foil can thereby be situated more visibly because of the shorter axial length of the holes, which facilitates reliable manipulation, in particular in the case of older people. In the version with the flat extensions which plunge into the slots, the suction tube is secured against rotation starting from the instant of the first insertion of the extensions; in the version with a sleeve, the same can be achieved by securing against rotation between suction tube and sleeve and by placing the sleeve on a non-circular hole rim. The cutting flanks situated in a protected, set-back manner can also be designed in relation to the hole of the carrier so that an optimum air entrance cross section to the cavity remains free because this cutting region of the suction tube has no longer anything to do with positioning and guiding it. That promotes not only the always uniform emptying of the cavity by the air flowing in freely from all sides, but also prevents residues of the powder accumulating in the suction tube after repeated use of the latter, as may occur, for example, in the air inlet channels of the prior published solution in accordance with OS 196 19 536. In regard to the longitudinal guidance or positioning of the suction tube, it proves advantageous that the suction tube can be guided in slots, situated on either side of the holes, of the carrier. A type of carriage-like displacement capability then exists.

If the piercing flanks are designed as flat, projecting extensions, they form an excellent protection for the cutting edge and any plunger blades. In addition, they ensure that large air entrance cross sections remain. Moreover, they open up progressive possibilities in regard to the releasable fitting of the suction tube to the carrier and its correct fitting for manipulation, even when not in use. The tongues, which serve as guide tongues during positioning and insertion of the suction tube into the holes, also make possible an advantageous configuration as a result of a pivotal fitting of the tongues to the blister pack carrier. That can also be utilized for a guided mobility, for example first into a position covering the holes in order then to descend into suction tube positioning free spaces situated below the slots. The corresponding slotted link is sited so that no contact takes place between the piercing flanks of the suction tube and sections of the carrier on the intervening path to the respective next correct suction position. In this way, the piercing or active perforation flank of the cutting edge is always protected. The positioning free spaces are advantageously designed as insertion channels proceeding from the slots. The guide tongues may each have a protrusion which can be inserted into the insertion channels. The final position of this insertion movement is the final piercing position. Provision is furthermore made that the suction tube has a plunger section which moves into the holes and which, set back with respect to the piercing flanks, is disposed in such a way that it supplements a linear guidance of the suction tube when the protrusions enter the insertion channels. In this connection it furthermore proves advantageous that those surfaces of the suction tube adjacent to the plunger section in the piercing position are placed on the regions to the side of the holes of the carrier. This results in a support for the tilt-free piercing position. Furthermore, the device is characterized by a lid of the carrier, which lid covers the suction tube which can be folded away.

A retention of the suction tube on the blister or carrier has the advantage that the suction tube is not used too long. By means of slots in the blister pack, into which slots the extensions of the suction tube have to plunge/plunge through, the blister can even be individualized for use.

A compact construction of the device can be achieved. Advantageously, the guidance between suction tube and carrier is such that the suction tube can be moved consecutively in two planes. This organization provides a double positioning, and specifically, transversely to the holes and in a piercing plane. A space-saving out-of-use position for the suction tube is achieved at the same time if the suction tube is moveable in one of the two planes both in a foldable and linear manner.

On the blister-pack side a likewise advantageous design is made possible in this connection: it consists, for example, in that the blister pack is folded into a bar of polygonal cross section with cavities situated on the inside and can be pushed into the carrier in a plurality of positions rotated around its longitudinal axis. Such a bar shape is space-saving. To accommodate the cavities the interior space produced during the folding is in any case used. That can extend to a contiguous contact of the cavities back to back, which results in a mutual support, given congruent alignment. In this connection, it is beneficial if the blister-pack bar can be pushed in the longitudinal direction into the carrier. This results in a logical utilization of the idea of longitudinal guidance. A spatially advantageous cross-sectional form of the blister-pack bar consists in that it has a square cross section and has a row of cavities on each of all four wide sides. Although the blister-pack bar also already has a certain stiffness solely as a result of the folding or acquires a trueness of shape, these properties can be increased further by enclosing the blister-pack hollow bar in an insertion cage which forms openings on all the side walls which coincide with the position of the cavities. The carrier is then fitted to it. There may be seven cavities for each wide side, for example as a weekly requirement of medication dosages. If a continuous contact of the back of the walls of the cavities is dispensed with, an advantageous measure may consist in that the carrier has a central bar which plunges into the internal cross section of the blister-pack hollow bar, at least the flank of said central bar which is adjacent to the suction tube being designed as supporting base for the underside of the cavities. Preferably, however, the central bar is designed so that all four flanks of the central bar are formed as supporting bases. That provides at the same time an internal guidance. In order to prevent the blister-pack hollow bar sliding out of the insertion cage surrounding it in a protective manner during the loading/reloading of the carrier, provision is made that the blister-pack hollow bar latches into a insertion limit position in the cage. This can involve simple latching nipples which latch into corresponding recesses. At the same time, it is furthermore advantageous if the (closed) end face of the insertion cage is provided with use symbols. While retaining the principle of longitudinal extension or bar shape, the carrier is also similarly formed. According to the achievement, that consists in that the carrier is of bar-shaped design and has a rectilinear row of suction tube passage holes on one side surface, which holes are situated congruently with respect to the blister-pack cavities. The holes are connected together by narrower, free cross sections. Instead of a carrier-side central bar, the appropriate stiffness of the prismatic blister pack may also proceed from the latter itself. This is achieved by a (solid) bar which shapes the blister-pack cavities as core piece and whose side surfaces comprise the blister-pack covering foil. In this way, there is a solid magazine. The latter can preferably be made of glass in order to comply with relevant storage requirements in regard to certain medication powders (suitable for storage in glass packages). Also conceivable are other materials, such as ceramic and solid plastic. In order to achieve the rotation advantage here as well, the circumstances described above are used as a basis. In this connection, it is also the case that the cavities of all the side surfaces are each situated on a common transverse plane of the core piece. The bar can then also embody the guide means for the suction tube so that suction tube and bar are thus also again an integral unit. That has the advantage that, when the (empty) blister is replaced, the suction tube is also replaced, which avoids one and the same suction tube being used for too long and, for example, becoming medically unsafe as a result of residues or the like. One form of the integral unit consists in this connection in that the suction tube is preferably seated on the bar or cage in "piggy-back" fashion in a stud/hole plug connection and, when the rod is pushed into the carrier, is transferred to the guide/guide grooves of the carrier, preferably with automatic detachment of the stud/hole plug connection. Under these circumstances, the suction tube remains on the carrier and can be folded into the insertion standby position, even if the bar is pulled out of the carrier, for example, in order to re-insert it after rotation. If a new bar (with filled cavities) is put into use, it can only be pushed into the carrier if the suction tube of the preceding bar is pulled out of the guides in the carrier in order then to dispose of it. In accordance with the claims, that is characterized in detail in that the suction tube is seated in a releasable connection on the bar or cage and the connection is automatically released when the bar or cage is pushed into the carrier, with the transfer of the suction tube to a guide in the carrier. In this connection, it proves advantageous that one flat side of the suction tube has studs which enter in a friction-locked manner into holes of the bar, core piece or cage. The frictional forces are adjusted so that the suction tube can be moved only deliberately from its straddling position. Specifically, an advantageous measure consists in that the release of the suction tube when it is transferred to the guide in the carrier is brought about by chamfering lead-in lifting protrusions in a row of teeth. Their significance is explained below. For the purpose of a space-saving accommodation of the suction tube when transversing the row of cavities, it is advantageous in this connection that the suction tube can be rotated around a transverse axis as a consequence of articulated arrangement on its guide tongues. The appropriate articulation ensures an oppositely directed folding over of the suction tube. In this connection, it proves advantageous at the same time that the tongues, which are disposed in pairs, are of rotationally symmetrical design and are supported in the folded-away position of the suction tube on the shoulders of the latter. Suction tube and tongues form a rigid unit. A design which is advantageous for use is provided in that the end wall of the cage is provided with authenticity sealing bridges positioned in accordance with the angle of the rotatability of the cage, of which the authenticity sealing bridge situated in each case adjacent to the lid can be destroyed by a lug in the lid during the closure movement of the latter. The user is thus able to read off which row of cavities is still filled. Such an authenticity sealing bridge can be of contrasting colour so that its absence is particularly conspicuous. A further measure for achieving a clear manipulation of the device is embodied in that the cap-shaped lid can be moved in the course of the folding/pushing movement into a lowered position situated on the other side of the rear housing end. The lid disappears in this way from the removal region and is also not hidden from view. In this connection, the technical means are such that the lid has a transversely projecting arm which is guided in an articulated and displaceable manner along the upper housing side and, in addition, is connected to the lower housing side by means of a connecting rod. In this connection, it is furthermore the case that a lid-side coupling point of the connecting rod can be displaced in a longitudinal slit in the lid. In this connection, the invention proposes that the arm is designed as a pair and each arm can be displaced with a guide stud in a guide slot in the housing towards the leading end of the housing. Bearing in mind the silhouette of the folded-away suction tube, the procedure is furthermore adopted that the guide slot at the rear housing end continues in a downwardly directed section in such a manner that, when the lid is opened, said section brings about a lifting or lowering movement of the lid which is such that its lid rim edge travels over the suction tube without contact. Taking up the significance of the row of teeth or teeth gaps, an advantageous development is characterized by a comb-like projecting row of teeth on each side wall of the housing, into whose gaps the suction tube is guided during the piercing movement of the suction tube. Finally, it is advantageous that the suction tube is latched in the downward-inserted position.

Furthermore, the carrier receiving the blister pack may continue in a mounting into which the unlatchable axial stumps enter and can be introduced as a whole with the blister pack into a lid-closed housing in such a way that fixtures which latch on the suction tube fold up the suction tube, swivelling it around the axial stumps, into a grippable position. The suction tube is thus ready for gripping. The axial stumps can be overcome in a latch fashion. The housing is in this case expediently a folding case. The said fixtures can be formed onto the inside of its lid. When the carrier is inserted/pushed in (plus blister attached to it), longitudinal ribs on the base of the lower part of the folding box pass between every two rows of cavities. Insertion slots in the carrier and blister are provided for the unsupported ends of the tongues at the apex of the longitudinal ribs, congruently with the individual slots of the carrier and blister.

The invention then proposes that the blister-pack covering film has insertion slots for extensions which are congruent with respect to the individual slots in the carrier and laterally adjacent to the cavities.

Another type of positioning aid plus blade protection is achieved in that the extension is designed as a sleeve which can be loosely displaced longitudinally on the insertion end of the suction tube. Such a tubular body provides a comprehensive protection of the exposed piercing flanks. In the pierced position, on the other hand, this does not impede the entrance of air into the cavity because the sleeve is then pushed back. In this connection, it is advantageous if the sleeve can be latched both in a pushed-forward position projecting beyond the piercing flanks and in a pushed-back position exposing the piercing flanks. The exposing position is not to be understood in the sense of a grippable or seizable exposure; on the contrary, the exposing pushed-back position is the piercing function position in which the cutting edges of the piercing flanks are therefore in the protective space of the cavity. It is furthermore proposed that the two latching positions are automatically entered during the insertion movement and withdrawal movement of the suction tube in the holes. There is virtually an automatic sleeve displacement derivable from the fitting of the suction tube, which fitting is suitable for operation. In this connection, the carrier is, so to speak, used as a counterbearing, which is structurally embodied by simple means in that the automatic entrance takes place by interaction with the rim of the suction-tube passage hole in the carrier. As a development, it is additionally proposed that the sleeve has, at the unsupported end, an external bead which interacts with the hole rim edge of the carrier and has, at the opposite end, an internal bead which interacts with latching steps on the suction tube. The appropriate latching capability of the sleeve is achieved by simple means in that the sleeve is of radially resilient design as a consequence of longitudinally directed slotting. In this connection, there is also the measure that two slot pairs proceeding from the sleeve ends are directed at one another up to a central circumferential bridge. This results, so to speak, in a double-arm double-pawl with folding axis provided by the remaining circumferential bridge. In addition, the circumferential bridge is interrupted by slots in the sleeve wall which are situated in a circumferentially offset manner. For the purpose of the releasing opening of the sleeve, the external bead forms a lead-in chamfer for the push-in movement. The entering end of the sleeve is thus forced into a constriction. A feature of the invention then consists in that the forcing inwards of the external bead contributes to a forcing outwards of the internal bead of the sleeve by the lead-in chamfers as a consequence of the double-arm construction. That takes place against the restoring force of the material of the sleeve. In order to move the latter back into its protective position with respect to the piercing flanks when the suction tube is separated from the carrier, it is proposed that the external bead is latched in an overcomable manner with respect to its insertion movement into the insertion limit position. A further advantageous feature of the invention then consists in that the slot or slots interrupting the circumferential bridge are at the same time passage cross sections for an additional air suction flow which travels above the carrier from the side into the main suction channel of the suction tube.

Figure 8:
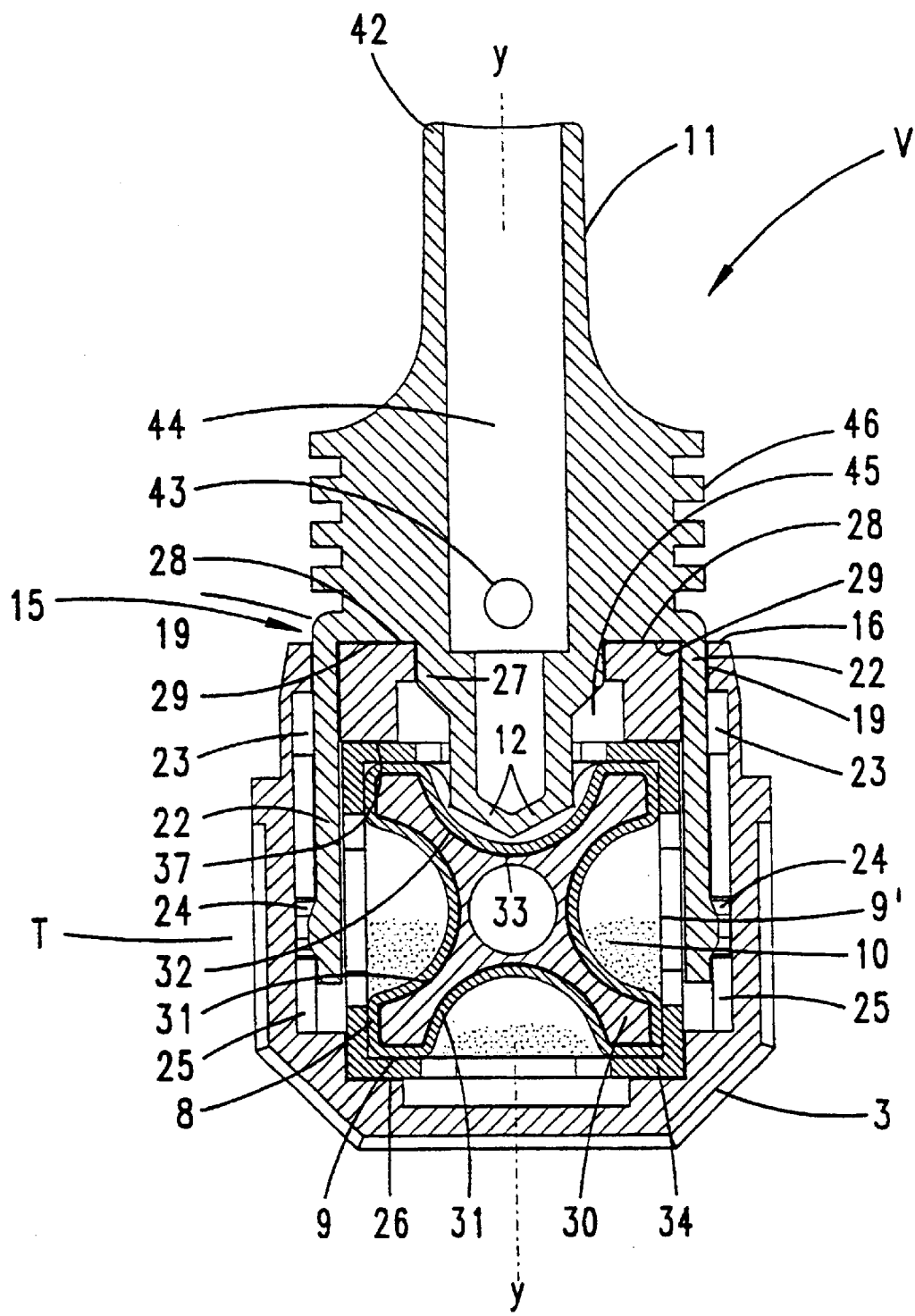

The subject matter of the invention is explained below by reference to a plurality of illustrative exemplary embodiments. In the drawings:

FIG. 1 shows a side view of the device according to the invention, and specifically, in approximately actual size, in accordance with the first exemplary embodiment, FIG. 2 shows a plan view of the latter, FIG. 3 shows a loading-side end face of the device, FIG. 4 shows a side view of the device with opened lid and still not completely fitted insertion cage, containing a blister pack hollow bar and with suction tube folded away, FIG. 5 shows a view as in FIG. 4, but with suction tube situated in the piercing position, that is to say erected and correct for use, FIG. 6 shows a plan view of FIG. 5, FIG. 7 shows the section along the line VII—VII in FIG. 6, on an enlarged scale and with the suction tube in displacement position, FIG. 8 shows a view corresponding to that of FIG. 7, now showing the piercing position, FIG. 9 shows the section along line IX—IX in FIG. 6, on an enlarged scale and illustrating a movement study of the suction tube fitted in a tipping-carriage fashion, FIG. 10 shows the section along the line X—X in FIG. 2, on an enlarged scale, FIG. 11 shows a sectional view as in FIG. 10, but with lid removed and suction tube situated in piercing position, FIG. 12 shows the plan view of a blister pack with covering foil sealing the cavities, FIG. 13 shows the blister pack folded into a hollow bar, FIG. 14 shows an end view of the blister pack hollow bar illustrating the folded profile, FIG. 15 shows a side view of an insertion cage which receives the blister pack hollow bar, FIG. 16 shows the plan view thereof, FIG. 17 shows an end view corresponding to FIG. 3, in this case of the insertion cage alone, FIG. 18 shows a side view of a bar which moulds the blister pack cavities as a centre piece, FIG. 19 shows the plan view thereof, FIG. 20 shows an end view as in FIG. 17, and FIG. 21 shows the section along the line XXI—XXI in FIG. 18, on an enlarged scale.

Figure 32:
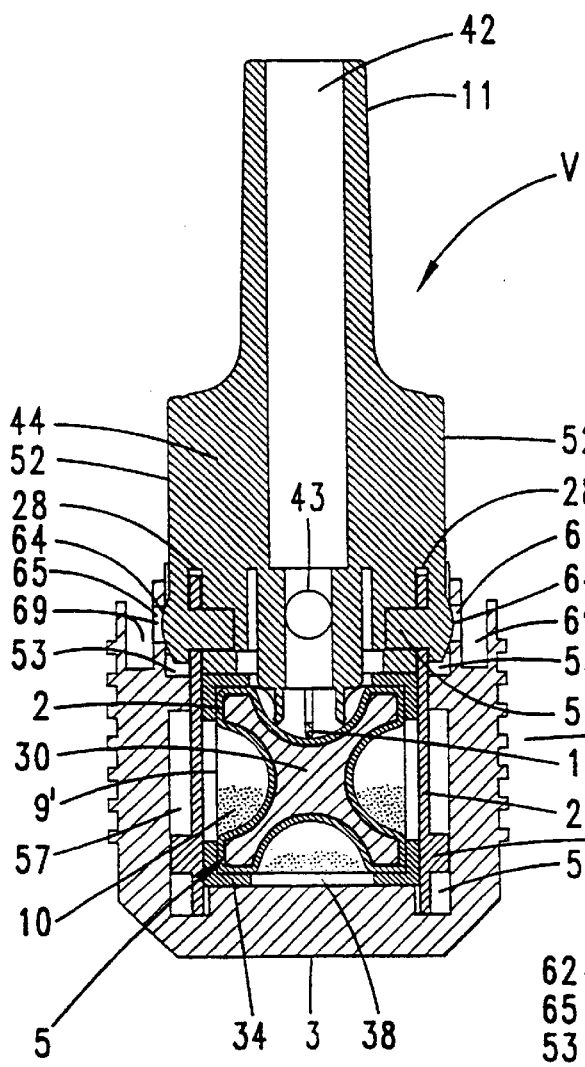
Figure 33:
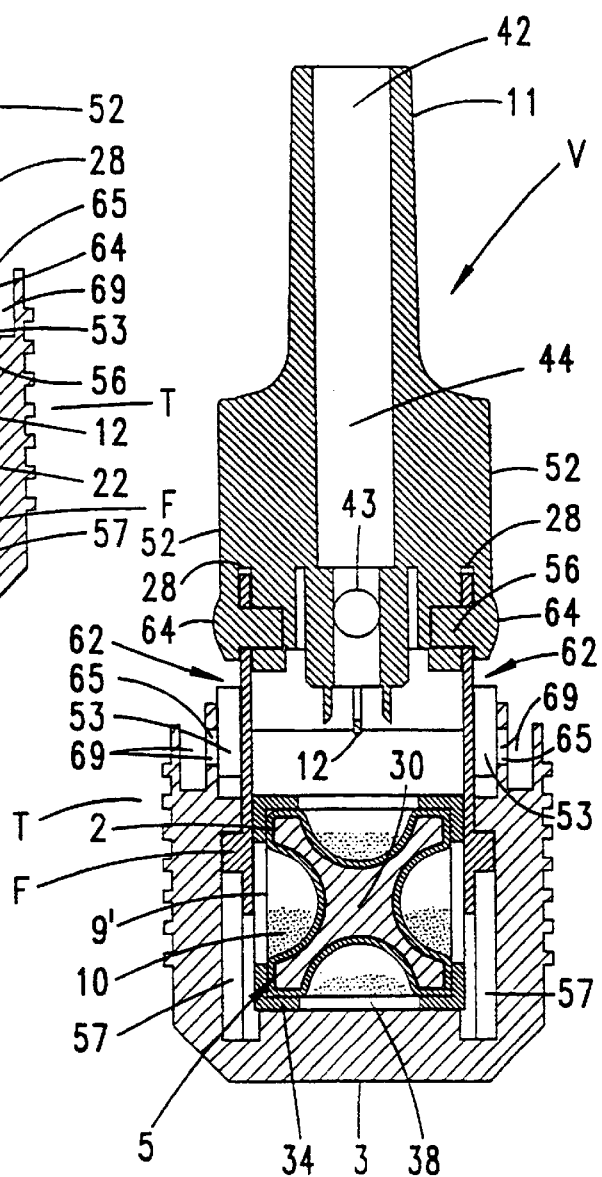
Figure 34:
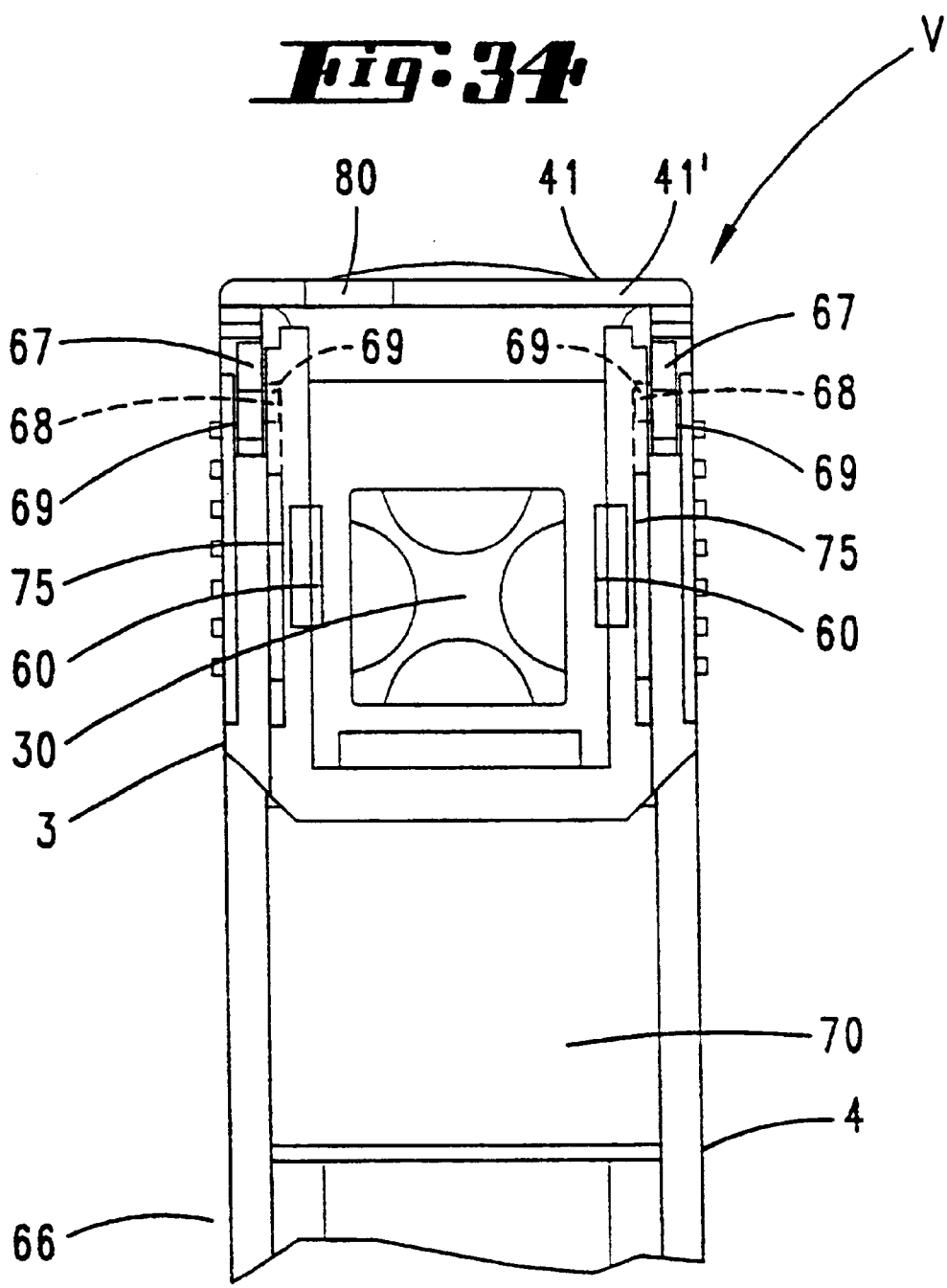
Figure 35:
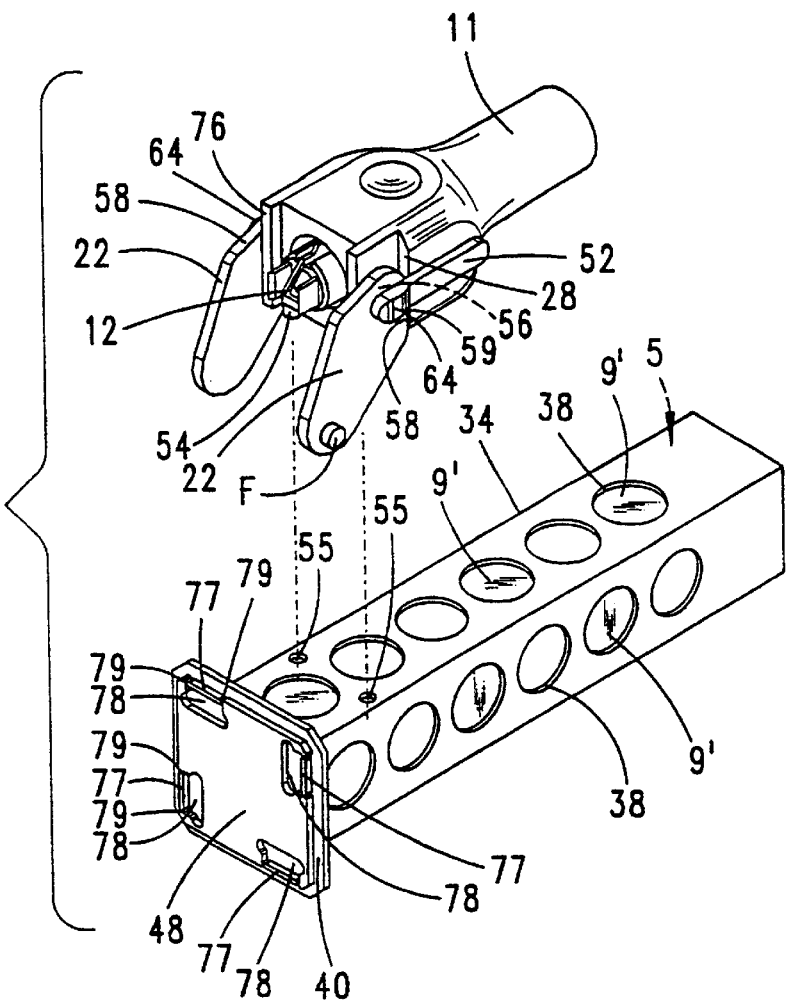
Figure 36:
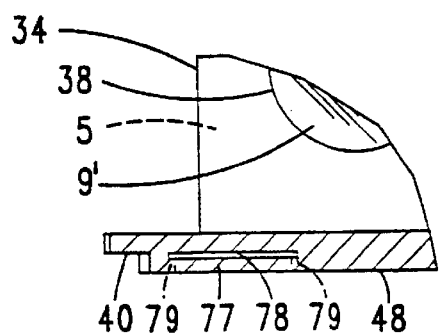
Figure 37:
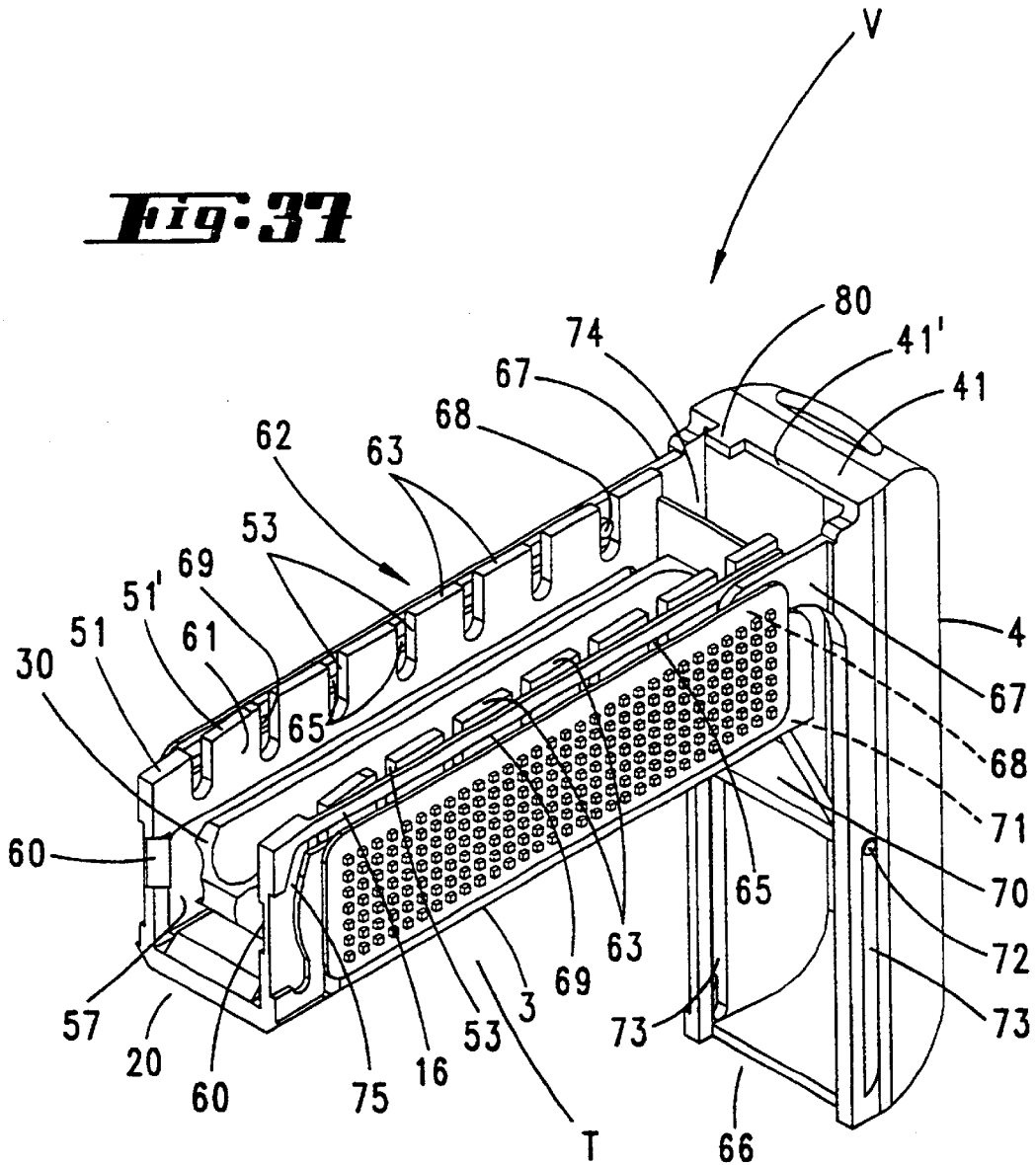
Figure 38:
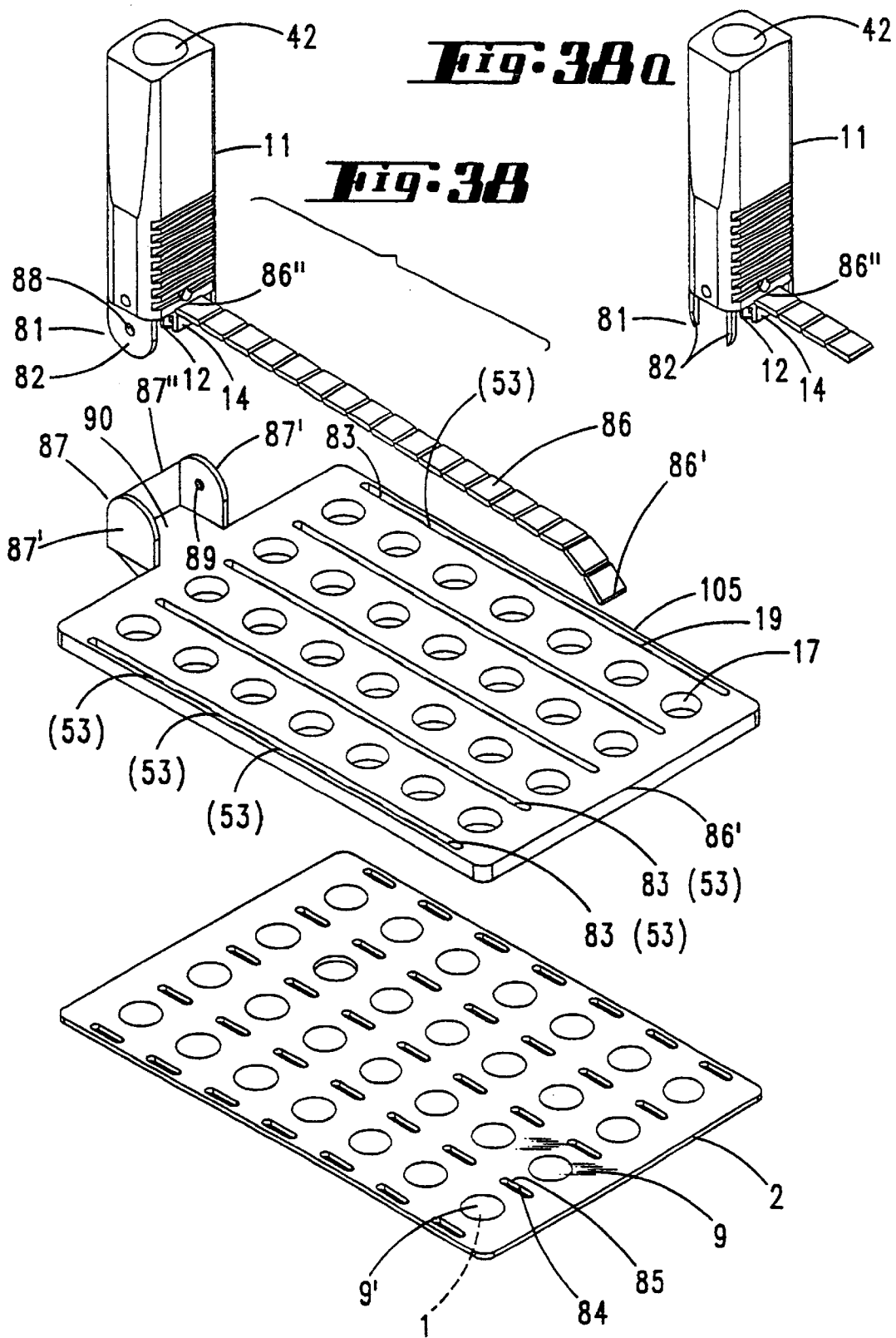
Figure 39:
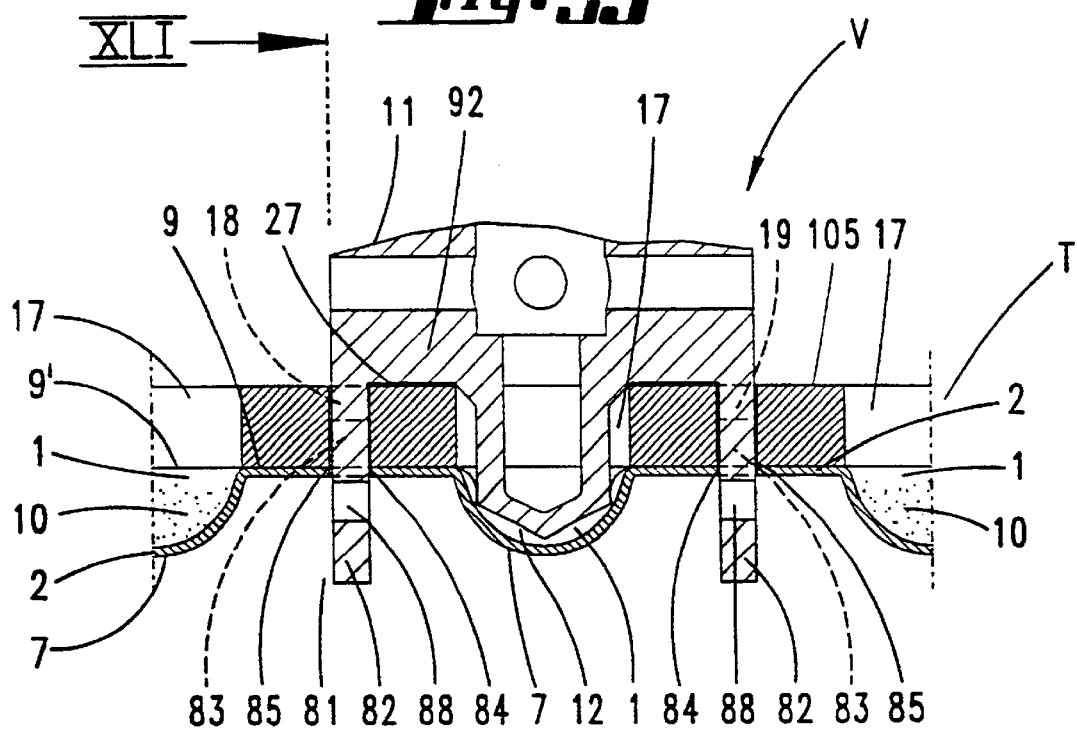
Figure 40:
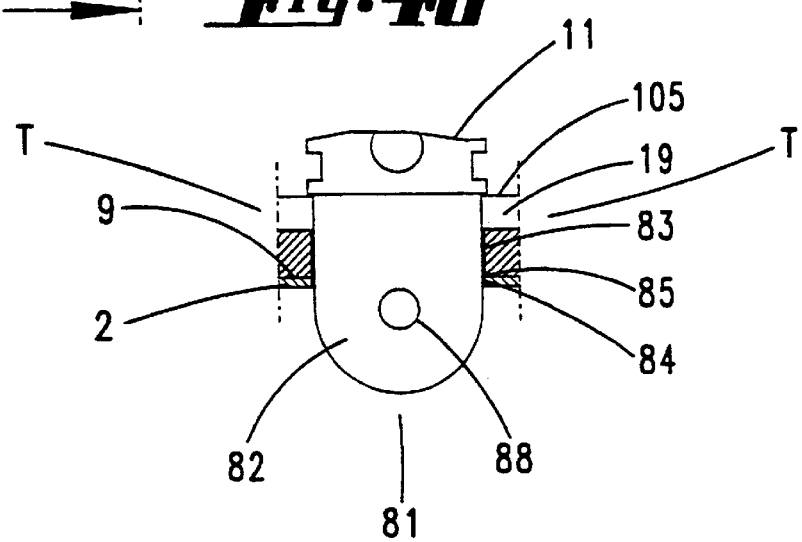
Figure 43:
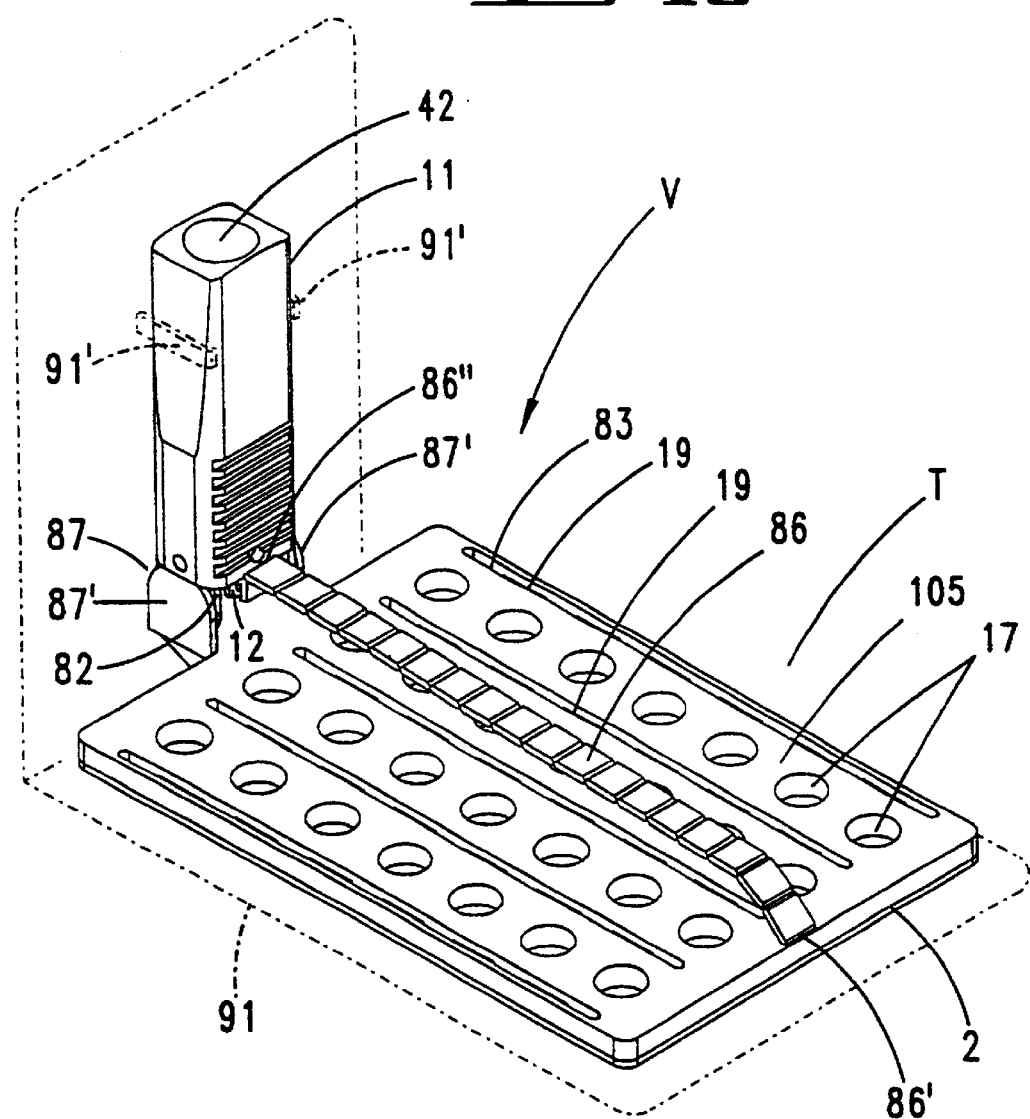
Figure 51:
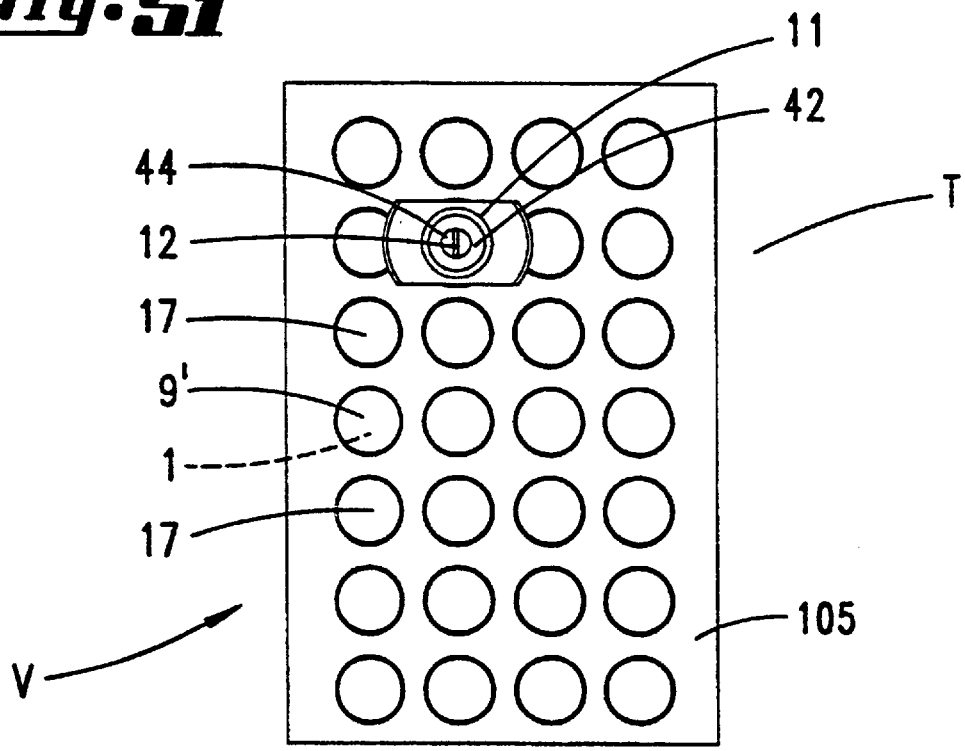
Figure 52:
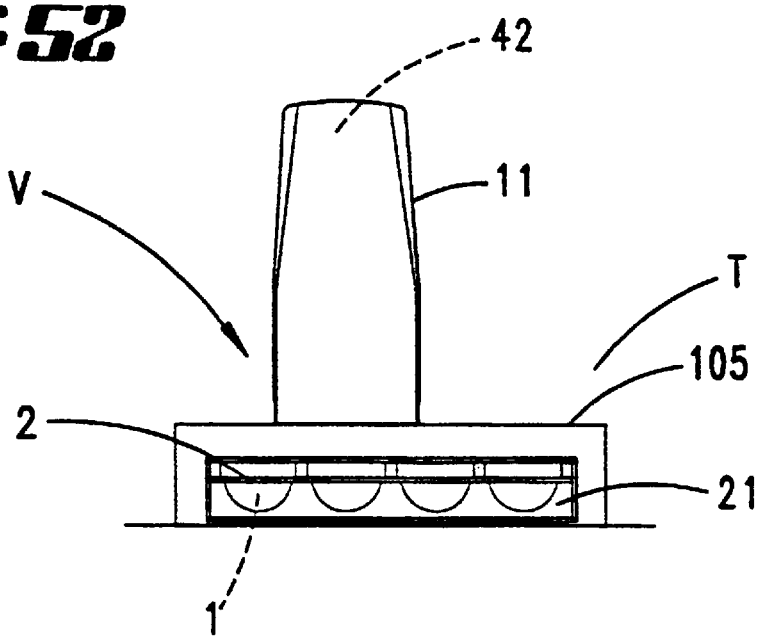

FIG. 22 shows a side view of a modified design as second exemplary embodiment,

FIG. 23 shows a development of the device in accordance with the second exemplary embodiment, and specifically in side view with lid closed, FIG. 24 shows the plan view thereof, FIG. 25 shows a loading-side end view of the device, FIG. 26 shows the other end view of the device, FIG. 27 shows the device in a loading position with the cage carrying the suction tube fitted to the housing in straddling fashion, with lid brought to lowered position under these circumstances, FIG. 28 shows the plan view thereof, FIG. 29 shows cage with suction tube in swivelling phase, FIG. 30 shows a view as in FIG. 29, but after removal of the connection between suction tube and cage or bar, FIG. 31 shows the device with suction tube set to the piercing position (with raised position correct for piercing shown in chain-dot line fashion), FIG. 32 shows the section along line XXXII—XXXII in FIG. 31, on an enlarged scale, FIG. 33 shows the section along line XXXIII—XXXIII in FIG. 31 with suction tube now shown in solid-line fashion, likewise on an enlarged scale, FIG. 34 shows the loading-side end view of the device, opened, FIG. 35 shows suction tube and cage in a position correct for coupling, diagrammatically, FIG. 36 shows a sectional detail in the region of one of the authenticity bridge seals, FIG. 37 shows the device correct for loading in perspective, FIG. 38 shows a third exemplary embodiment, and FIG. 38a shows the extensions/tongues 82 reduced to the corners of a square, FIG. 39 shows an enlarged section with suction tube inserted, FIG. 40 shows a cross section thereof along the line XLI—XLI in FIG. 39, FIG. 41 shows said device with suction tube folded away, again in a diagrammatic view, FIG. 42 shows a view corresponding to FIG. 41, and specifically with suction tube situated in an intermediate folding position, FIG. 43 shows a view corresponding to FIG. 41 with suction tube brought to a gripping position brought about by entrainment members of a surrounding housing which can be swung open, FIG. 43a shows a perspective view of such a housing which can be swung open, FIG. 43b shows a cross section through a sub-region of the housing, with carrier lying in position plus blister and inserted suction tube, FIG. 44 shows the plan view of FIG. 43, FIG. 45 shows the device in accordance with a fourth exemplary embodiment in perspective, with suction tube and sleeve positioned in the correct direction for insertion, FIG. 46 shows the sleeve protecting the piercing flanks in a perspective single view, FIG. 47 shows a section through the coupling region of the suction tube with the sleeve placed in position, FIG. 48 shows the latter with the sleeve released for its retraction, FIG. 49 shows an enlargement of a part of FIG. 48, FIG. 50 shows the suction tube in completed piercing position, FIG. 51 shows the plan view of FIG. 52 and FIG. 52 shows an end view of FIG. 51.

The device V shown for emptying powder-containing cavities 1 of blister packs 2 by suction has a housing 3. The latter can be closed with a lid. In the first exemplary embodiment, the lid has the reference symbol 4.

In the first and second embodiment, the housing 3 is an elongated carrier T. The latter is of bar-shaped design and longitudinally hollowed. The bar length corresponds to about three to six times the bar width. Preferably, a square cross section exists in this respect at least for the hollowed-out section.

The carrier T can be accessed for loading from its one end face. The other end face is closed.

The loading material is a blister pack 2 matched in its cross section to the hollowed-out section. In this case, said blister pack has accordingly a bar shape (reference should be made to FIGS. 13 and 14).

Proceeding from a card-shaped top view, the blister pack 2 is folded to form a hollow bar 5. The folding takes place transversely to the longer side of the blister pack 2, and specifically around a longitudinal centre axis x—x. As can be seen from FIG. 12, four longitudinal strips of equal area are defined by means of fold lines 6. This results in a polygonal cross section, in this case in a square cross section.

The folding direction resulting in a box-type profile is chosen so that the cavities 1 project into the interior of the blister-pack bar 5.

The cavities 1 shown are cup-shaped recesses 7 in a thin aluminium/plastic composite foil 8.

For the purpose of the equipment, care has been taken that one linear row of cavities 1 exists in each case on all four wide sides of the longitudinal strips formed. Specifically, there are seven cavities 1 equally spaced longitudinally. The periodicity is equal on all the longitudinal strips.

The cavities 1 are sealed by a piercable covering foil 9. The contained powder, shown as a pattern of dots, is denoted by 10. Spatially, it occupies only a partial volume of the cavity 1.

The blister-pack hollow bar 5 is pushed in proceeding in the longitudinal direction of the carrier T, and specifically, in accordance with the drawing, from the left side of the device V. In view of the square cross section of the blister-pack hollow bar 5, the latter can be turned around its longitudinal centre axis x—x suitably for emptying by suction in each case through 90° C., covering the requirement of four weeks.

The residue-free emptying by suction of the powder-containing cavities 1 takes place via a suction tube 11. The latter is designed so that its leading end, adjacent to the cavity 1, pierces the covering foil 9. For this purpose, the suction tube 11 has a cutting edge 12 in the form of a centrally situated blade-type flank. The latter is designed in the form of a curved blade and pierces the unsupported stretched section 9' of the covering foil 9 of the cavity 1. The configuration in this respect is in detail such that the centrally situated flank having a curved section projecting beyond a flattened end face 13 of the suction tube 11 is designed with cutting edges situated in pointed-roof fashion with respect to one another. The point is centrally situated.

Radially (laterally) adjacent flanks are fitted as plunger blades 14 to said centrally situated, cutting-edge-forming flank. Said plunger blades dislodge those surface sections of the covering foil cut free. They are somewhat shorter than the cutting edge 12 and widen the gap cut in the unsupported stretched section 9'. Further details are to be found in the non-prepublished German Patent Application 197 57 207.3. The disclosure content of the latter is included here to the full, also for the purpose of including features of said documents in the claims of the present application.

An advantageous fitting of the suction tube 11 on the carrier T is achieved by means of the longitudinal guide 15 shown. The latter is designed for a carriage-like, linear movement of the suction tube 11. For this purpose, the bar-shaped carrier T has a perforation for the purpose of access on a side surface 16. The latter is formed as a rectilinear row of suction tube passage holes 17. Said holes 17 are congruent with the blister-pack cavities 1 extending thereunder. The holes 17 are interconnected by means of wasp-waist-type recesses, this being in the form of a longitudinal hole having corrugated flanks. The correspondingly narrower cross sections between two holes 17 in each case have the reference symbol 18.

The track-providing longitudinal guide 15 for the suction tube 11 comprises slots 19 of the carrier T which lie on either side of the row of holes 17. The slots 19 extend in parallel and as close as possible to the rim of the holes 17 or, in the case of only one row of holes, near the rim of the side surface 16. This results in a good tilt-free guidance for the suction tube 11. The slots 19 aligned in parallel are closed in the region of the loading opening 20 and open in the region of the other end face for the purpose of assembly. In the latter case, however, it is necessary to overcome a latching protrusion 21 which makes the slot slightly narrower so that this region is normally felt to be a stop and also acts as such in the case of moderate forces.

Extensions in the form of tongues 22 running in the slots 19 are the guided part of the suction tube 1. They are formed in fin-like fashion on the suction tube 11 on both sides of the formed cutting head. The guide tongues 22 extend in parallel and plunge relatively deeply into the slots 19. They are adjacent to the cutting edges and plunger blades 14 at a distance and project axially forward beyond the plunger blades and cutting edge.

In the wall of the two adjoining side surfaces of the carrier T, longitudinal grooves 23 extend underneath the slot 19. Reference should be made to FIG. 9.

Outwardly directed protrusions 24 formed on the unsupported ends of the tongues 22 slide in the longitudinal grooves 23. Said protrusions simultaneously guide and retain the suction tube 11 in a trapped manner on the carrier T.

The said protrusions 24 are arranged spatially so that the suction tube 11 can be folded away into a supported position in a precisely aligned manner above the holes 17. The displacement movement of the suction tube 11 in the direction of the blister-pack hollow bar 5 is simultaneously the perforation movement. In order to achieve piercing displacement proceeding in the direction of the cavity 1, positioning free spaces 25 are shaped out underneath the slots 19. Said positioning free spaces as insertion channels extend from the groove 23 in the direction of a base 26 formed by the lower wall of the carrier T. FIG. 9 shows an alignment of the suction tube 11, which alignment reproduces the piercing position. This is the central position. The corresponding slotted-link guide for the parallel protrusions 24 is such that, on the intervening path between two piercing positions, the cutting edge 11 makes no contact with parts of the carrier T or of the blister-pack hollow bar 5, except for vertical guidance for the plunger section 27 of the suction tube 11 extending on the piercing side to the curved blade, which vertical guidance is suitable for perforation and is non-rotatable in a shape-locked manner.

Everything is achieved by a guidance between the suction tube 11 and carrier T in such a way that the suction tube 11 can be moved consecutively in two planes situated at right angles to one another. Said planes are a horizontal plane E1, responsible for the positioning jump to the next cavity, and an adjacent vertical plane E2 in which the cavity 1 is opened in the final phase. Said two planes E1 and E2 are indicated by double arrows. The planes come about by corresponding tracking between protrusions 24 and groove 23 and insertion channels.

Cutting edge and plunger blades are situated in a set-back manner and protected even when not in use, for example in a folded-away position of the suction tube 11 explained below. In this connection, an advantageous configuration is also achieved in that, in one of the two planes E1, E2, the suction tube can be displaced and guided both in a foldable and a linear manner. The suction tube 11 can be pushed to lie on its belly in the plane E1. In that case, the protrusion 24 is guided in the plane E1. The folding-arc plane is denoted by E3 in FIG. 9.

The plunger section 27 entering the holes 17 is designed or fitted in such a way that it supplements a linear guidance of the suction tube 11 when the protrusions 24 enter the insertion channels (that is to say, positioning gaps 25) and slide therein in a guided manner towards the base. However, they do not make contact there in the region of the slot ends since the end region acts as a switching zone for the protrusions 24 during the tilting of the suction tube 11.

On the contrary the seating position, ensuring the vertical upright position, of the suction tube 11 has priority. For this purpose, the base region of the guide tongues. 22 is given shoulders 28. The latter extend to the side of the stub-shaped plunger section 27 of the suction tube 11. They extend perpendicularly to the vertical longitudinal centre axis y-y of the suction tube 11 shown in FIG. 7. The surfaces forming the shoulders 28 are set down in the piercing position (FIG. 8) in a plane-parallel manner on the regions 29 of the corresponding side surface 16, that is to say on both sides of the holes 17 of the carrier T. This is shown in FIG. 8.

The carrier T contains a centre bar 30. The latter has its root internally in the right-hand end wall of the device V. It (30) extends in a projecting unsupported manner virtually over the entire length of the carrier T. It plunges into the contour-matching internal cross section 31 (cf. FIG. 14) of the blister-pack hollow bar 5 when pushed in.

At least one flank 32 adjacent to the suction tube 11 acts as a supporting base for the cavity underside 33 at that position. Preferably, all four flanks, offset at an equal angle, of the centre bar 30 are moulded with the formation of such a supporting base. This involves longitudinal flutes which are designed to match the silhouettes of the dome-shaped contour of the recesses 7. This is based on a rotationally symmetrical profile.

If the folded profile of the blister-pack bar 5 is not closed, it can be sheathed. In accordance with the diagrammatic view, this is embodied in the fitting of a cage 34. The latter is formed as an insertion pocket having a square cross section. Although a friction-locked fitting of the two parts 5, 34 is conceivable, the achievement according to the invention provides for latching. The corresponding latching between blister-pack hollow bar 5 and cage 34 takes place in the insertion limit position of the blister-pack hollow bar 5.

The latching means can be a nipple 35 on the male moulding which latches into a congruently situated recess or perforation 36 in the blister-pack hollow bar 5. Depending on the application purpose of the cage 34, that is to say whether it is provided as a disposable or permanently usable part, a reversible or irreversible latching 35/36 may be involved. The technical basic design of allowing the user to convert the blister pack 2 into a hollow bar shape favours permanent use of the cage 34. In this case, the card-shaped blister pack 2 could be supplied in a space-saving stacked manner.

All four side walls 37 of the insertion cage 34 are provided with openings 38 and free cross sections 39 which connect them. There is an elongated-hole contour as has been described in depth in regard to the carrier T. The mask is identical. Thus, the cutting edge of the plunger section 27 can also engage through this congruently situated elongated hole and reach the underlying cavities 1 unimpeded since the openings 38 plus cross sections 39 correspond to the holes 17 plus cross sections 18 in terms of area. The plunger blades 14 are somewhat narrower than the cross sections 39.

With or without insertion cage 34, the piercing cutting flank, that is to say cutting edge 12, terminates just above the base-forming inner wall of the cavity 1 or the supporting-base surface underneath, i.e. flank 32 of the centre bar 30 of the insertion cage 34 to protect the cutting edge against wear.

The insertion cage 34 is closed on the left-hand side by an end wall 40. The latter forms the insertion-limiting stop for the hollow bar 5 on the inside if there is no latching device 35/36.

Said end wall 40 then projects beyond the cross section of the rod-shaped sheath section of the cage 34 on all sides so that an insertion stop on the outside can be used as a result in the region of the loading opening 20 of the carrier T.

The end wall 40 also has, however, a more far-reaching function: this is that the said peripheral overhang forms a barrier and can be engaged over by the lid 4 of the device V on the lid side. The end wall of the lid 4 which engages over is denoted as 41. It secures the unit 5/34 in this way against sliding-out of the carrier T when not in use.

With the device V closed, the folded-away suction tube 11 is covered the by lid while resting on the upper side surface 16 of the carrier T. In this position, the protrusions 24 are situated in the longitudinal grooves 23.

The lid 4 has a markedly convexly arched surface with the zenith situated in the cross-sectional centre. This region is thus the most favourable for the space-saving folded-away position of the suction tube 11.

As can be seen from FIG. 6, the flat wall suitable for the mouth of the mouthpiece opening 42 assumes an elliptical wall shape in cross section. The longer elliptical axis extends in the longitudinal direction of the carrier T. This results in a position suitable for the mouth which is such that the device V can be held in the hand like a mouth organ in order in this way to be able to perform the suction action comfortably.

The emptying of the powder-containing cavity 1 by suction takes place with the aid of an additional air suction stream Z which entrains the powder 10 and which proceeds via transverse ventilation holes 43 in the suction tube 11. These extend in a diametrically opposite position and make an internal flow connection to the main channel 44 of the suction tube 11. As a result of close vicinity to the side surface 16 and an ample peripheral zone external recessing, the transverse ventilation holes 43 cannot be held in a closed manner either by gripping fingers of the hand in use or by parts of the lip of the mouth. Incidentally, additional air enters via the entire surroundings 45, to be kept very large, of the plunger section 27. To increase the gripping capacity of the suction tube 11, it is roughened on the outer surface, i.e. with annular ribs. The ribbing is denoted by 46.

The viewing side of the basically square end wall 40 of the cage 34 is provided with use symbols 47. These are numbers 1 to 4. From these the user can read off which cavity row still contains stock assuming, of course, that a numerically increasing transfer sequence is used.

It can furthermore be seen that the said end wall 40 has a square plateau 48 which is centrally situated. This exposed plateau 48 interacts by way of its side walls situated parallel to the square with that rim of the end wall 41 of the lid 4 which is oriented in the direction of the housing 3. This results in a type of key function. The "key" can be varied so that in each case only the medications or magazines intended for the treatment are used.

The requirements described also apply to the solid magazine shown in FIGS. 18 to 21. Said magazine is inherently stiffened, without fitting the cage 34 described above. The appropriate stiffening is achieved by a bar which moulds the blister-pack cavities 1 as core piece 49. The latter has a square cross section. Said core piece 49 which forms the solid magazine can be rotated in the manner described. It is also adapted in terms of cross section for insertion, suitable for operation, into the carrier T of the device V.

The side surfaces 50 of the bar-shaped core piece 49 are covered with the usual covering foil 9. This can be applied by gluing. The reference numerals are used analogously.

As FIG. 21 illustrates, the blister-pack cavities 1 are each disposed on a common transverse plane of the core piece 49. This applies to the whole row of cavities.

The core piece 49 is composed of glass. Its manufacture from ceramic or highly crystalline plastic is likewise conceivable.

In the modified solution of FIG. 22, the suction tube 11 is seated on the blister-pack bar 5 which may also be solidly formed like the core piece 49. For this purpose, the one flat side of the suction tube 11 has two studs which enter holes in the bar in a friction-locked manner. If the bar 5 is pushed into the carrier, the guide projections F are trapped in the grooves on the inside walls of the carrier T and, simultaneously, the suction tube is raised over the bevels 51 as a result, for example, of the ribs 52 being lifted with the separation of the stub/hole connection. The suction tube is now guided on the carrier T and can be swivelled in order to arrive at the standby position for piercing the foil section. The lateral ribs 52 of the suction tube 11 are guided during lowering (piercing) into the tooth gaps 53 of the carrier T.

The development of the device V, which development is based on the modified solutions in accordance with the second exemplary embodiment, is explained below in detail starting from FIG. 23. In this connection, the reference numerals are applied analogously provided there is correspondence with the designs described above, this being done in some cases without repetition in the text.

A coupling means between suction tube 11 and the bar 5, more precisely the cage 34, can now also be seen in FIGS. 27 to 30. The studs projecting perpendicularly at the one flat side of the suction tube 11 have the reference symbol 54. When the suction tube is laid flat on the upper side, they are inserted into congruently disposed hollow sections or holes 55 in the cage 34. There is a friction locking which can be overcome if specifically desired.

The cage 34 fitted with the bar also forms here the vehicle for a transfer of the suction tube 11 to the carrier T.

Here, again, guide tongues 22, which in accordance with a development are, however, fitted in an articulated manner to the suction tube 11 proceed from the two adjacent flat sides of the suction tube 11 which are situated in a space-parallel manner. The corresponding transverse axis has the reference symbol 56. In terms of plane, it is situated in the transverse centre plane of the symmetrically designed suction tube.

The tongues 22 are designed as rotationally symmetrical and permit the folding over of the suction tube 11 around the transverse axis 56 so that the suction tube can assume both a folded-away direction in which its mouthpiece opening 42 points in the direction for insertion of the cage 34 and also in the opposite direction.

The transfer takes place in the region of a guide on the housing side which is formed as grooves 57 on the inside walls of the carrier T. Guide projections F of the tongues 22 engage in said grooves 57. These are projecting cylindrical stumps. They are situated at the unsupported ends of the two tongues 22. Their position with regard to the loading opening 20 of the housing 3 is defined. In the folded-away position of the suction tube 11, the shoulder 28 of the latter, in particular, encounters a counter shoulder 58 of the tongues 22 which in turn counterbear against a collar-forming back of the end wall 40 of the cage 34. The tongue-side end is denoted by 59. Formed in a similar manner on both sides of an imaginary line which crosses the guide projection F and the transverse axis 56 is a second counter shoulder 58 and a second stop end 59 owing to the rotationally symmetrical structure. The line extends at an angle of 45° to the insertion direction of the cage 34.

Because of the supported configuration shown in FIG. 27, the guide projection F, more precisely its cylindrical stump, retains a longitudinal guidance alignment in whose path there is situated a latching projection 60 which can be overcome in both directions if desired. Said latching projection is mounted in front of the groove 57. When the latching projection 60 is passed, the stud connection 54/55 is broken.

If the cage 34 is then pulled off together with bar 5, the suction tube 11 remains retained on the carrier T by means of the tongues 22. The cage 34 can now be rotated and inserted again. A complete detachment of the suction tube is, on the other hand, also always possible, for example to insert the next bar 5 or cage 34 carrying a fresh suction tube 11.

The detachment of the suction tube 11 when it is transferred to the guide, that is to say grooves 57 of the carrier T, is effected by means of a lifting protrusion 61 on the feed side in a tooth row 62. The teeth 63 of the latter leave tooth gaps 53 between them. In the present development, the tooth gaps 53 also function as guide paths for the piercing movement of the suction tube 11, which guide paths are aligned perpendicularly with respect to the insertion movement of the cage 34. Here, again, the guide elements on the suction-tube side are the ribs 52. The tooth gaps 53 are disposed in accordance with the spacing of the blister-pack cavities 1, that is to say, they are situated at appropriate intervals.

The ribs 52 which are raised on the paired lifting protrusion 61, the latter being formed as bevelled first tooth 63 in the tooth row 62 on the head side, reach, subsequently to this lifting-out phase shown in FIG. 29, a position in which the lower longitudinal side of the straight ribs 52 is guided and supported on the linearly aligned heads of the subsequent teeth 63 of the tooth row 62. Here, again, the bevel is denoted by 51. The total rising path on the protrusion 61, including that of an upstream housing-side protrusion section 51' corresponds to the vertical length of the stud or studs 54. Accordingly, a complete lifting oaf the studs 54 out of their holes 55 occurs.

In accordance with a development, the rib 52 continues on the outside into a latching protrusion 64 in the direction of the transverse axis 56. The latching protrusion projects on the transverse side and interacts with a latching recess 65. The latter is situated in the region of the base of the tooth gaps 53 (cf. FIG. 32).

While the cap-shaped lid 4 in FIG. 22 is fitted to the housing 3 in a foldable manner (it can be moved to a book-cover-like folded-out position), the development in accordance with FIG. 23 et seq. additionally provides also a folded-away position. This provides a free space on the upper side which assists loading and unloading and also use and even provides a front holding handle 66.

For this purpose, the lid 4 is moved in the course of the folding/sliding movement into a lowered position situated beyond the rear housing end, that is to say the loading opening 20. A good two thirds of the length of the lid projects as a holding handle 66 on the underside of the housing 3.

The folding-away opening takes place in a forcibly controlled manner by means of articulating polygon between housing 3 and lid 4. In this connection, the displacement path of the lid 4 is such that the lid further takes account of the suction tube 11 set to the folded-away position as a protrusion above the upper side of the housing 3, in terms of outline, so that no contact occurs. In this connection, the procedure is in detail such that the lid 4 has an arm which projects transversely and which is formed in pairs. It comprises fork-shaped projections which start at the rim side of the cap-shaped lid 4, are situated in line with the longitudinal side walls of the lid and project transversely to the longitudinal extension of the lid. Situated in the end region of the arm 67 is a guide stud 68. The latter engages in a guide slot 69 of the housing 3. The latter extends over almost the entire length of the housing and is used not only for the displacement guidance, but also to form the articulation, this being for the purpose of the folding movement indicated.

The guide slot 69 extends along the upper housing side, and specifically, crossing the plane of the tooth gaps 53 which provide the latching recesses 65 in the form of window-like penetration areas for the latching protrusions 64.

In addition, the lid 4 is connected via a connecting rod 70 to the housing 3, via a fixed coupling point 71 on the housing side and via a displaceable coupling point 72 on the lid side.

Both are formed as axial stumps. For the purpose of the displaceability of the coupling point 72, the lid 4 has, near its rim, a longitudinal slot 73 extending parallel to the rim of the lid. Said longitudinal slot is of a length such that, in the position folded in the closure direction against the end face of the housing 3 at that point, the connecting rod 70 also permits the lid 4 to travel further into the closure position in which the end wall 41 of the lid 4 associated with the loading opening 20 is placed in a sealing manner in front of the loading opening 20 and latches, for example, at that point. Under these circumstances, the connecting rod 70 is swivelled into an end-face niche 74 of the housing 3.

The coupling point denoted 71 is situated near the base 26 of the housing 3.

The guide slot 69 continues at the rear housing end into a downwardly directed section 75. The latter extends virtually to the base 26. It is formed transversely with respect to the longitudinal extension of the housing 3 as a convexly extending arc. With respect to the cap movement, the latter has a guiding outwards action, and specifically, such that the section 75 results in a respective raising or lowering movement, when the lid 4 is displaced, and specifically, such that its lid rim edge 41' travels without making contact over the suction tube 11 coupled near the end of the cage 34 into the folded-away position. Accordingly, no contact at all therefore occurs between the lid 4 and the exposed edge 76 of the base region of the folded-away suction tube 11.

In conjunction with the folding movement of the lid 4, the end wall 40 of the cage 34 is designed to form an indication of use or, alternatively, a guarantee of genuineness. For this purpose, authenticity bridge seals 77 positioned in accordance with the angle of rotatability of the cage 34 are formed on the end wall 40. They extend in the plateau 48. They are situated accessibly beyond the plateau rim. There are strips which seal the entrance of inwardly directed recesses 78 which hang over end-side predetermined breaking points 79 at the edge of the recess 78.

The outside of the authenticity bridge seals 77 is situated within the range of action of a lug 80 of the lid 4. The lug is a projection which projects beyond the rim edge 41' of the lid 4 and which, in the final stage of the closure movement of the lid, causes the authenticity bridge seal 77 "to collapse", i.e. break out.

Such an authenticity sealing bridge 77 can be made conspicuous, that is to say to contrast optically and visually with the colour of the end wall 40. It is then immediately obvious which row of cavities has been used or emptied.

The openings 38 in the cage 34 may be of isolated design, as emerges, for example, from FIG. 34;

Also in the case of the development attention has been paid to displacement of the suction tube 11 which avoids contact with the cutting edge 12. The grooves 57 have been matched in height to the vertical movement of the suction tube. A guiding alignment of the suction tube with the tooth gaps 53 always has priority. In this position, the cutting edge 14 overlaps the covering foil 9 or the unsupported stretched section 9', respectively, in a suitable manner for piercing.

The third exemplary embodiment (FIGS. 38 to 44) shows a structurally modified unit. This embodiment it is based on using the slots 19 of the carrier T of the exemplary embodiments explained above. The tongue positioning is also included in the present technical concept. Extensions 81 extend at a distance to the side of the piercing flanks of the suction tube 11, of which flanks a central one also forms the cutting edge 12, again in the form of a curved blade and the two adjacent flanks act as plunger blades 14 which push aside the shreds of covering foil.

The extensions 81 are designed in the form of tongues 82. At the end of the piercing mandrel, they give the suction tube 11 the form of a fork head. The tongues 82 are disposed so that the top of a finger of a human hand does not reach into the fork space, that is to say no contamination or damage occurs in this respect to the piercing flanks. The tongues 82 project axially and rigidly beyond the plunger blades and cutting edge.

The plate 105 of the carrier T is approximately equal to the larger outline of a cigarette box and has the holes 17 positioned in a plurality of rows (for example, four) and even more (for example, seven) lines and slots 19 which extend on the upper side parallel to the rows. Said slots extend as guide rails or guide grooves at the side of the rows of the suction tube passage holes 17 and allow a convenient preorientation of the suction tube. The tongues 82 thus undertake the said function during positioning and insertion of the suction tube 11 into the holes 17.

The fork-prong-like continuations 81, or the tongues 82 which embody them, are of an axial projection length which is such that, when in the insertion position in the slots 19, the curved-blade cutting edge 12 and also the laterally adjacent, somewhat shorter plunger blades 14 do not make contact with the upper side of the plate 105, that is to say they cannot be damaged. The entrance into the cavity 1 is only possible if the suction tube 11 is positioned suitably for piercing. This position is defined by individual slots denoted as slots 83 in the carrier T and proceed downwards from the base of the slots 19. Said slots 83 are consequently also situated at the side of the suction tube passage holes 17, optionally in pairs. A locating-pin-type, and consequently precise, coupling situation results. For this purpose alone, a lateral extension 81 alone may also be sufficient. The construction in pairs serves, however, a purpose explained below. The slots 83 disposed in the plate 105 are also comparable in design and function to the tooth gaps 53 explained above, which are entered in that case by the lateral ribs 52 of the suction tube 11.

Plate 105 and blister pack 2 are joined together. The plate 105 extends like a mask or a perforated sieve over the blister pack 2. In the region of the four corners of the carrier, upwardly projecting pins St pass in a retaining manner through holes L of the blister 2 (see FIG. 43b) and possibly down into holes L' in the lower part. The holes 17 are situated precisely above the cavities 1. The individual slots 83 proceeding from the base of the slots 19 are situated congruently with respect to each insertion slot 84 of the blister pack 2. Expediently, the covering foil 9 is also congruently slotted in this manner. Its insertion slot is denoted by 85. The slots 83, 85, 84 are all engaged through by the tongue 82. The latter finally enters in an unsupportedly projecting manner between the recesses 7 in the blister pack 2 which form the cavities 1. Consequently, the latter is individualized for the appropriate use with respect to the suction tube.

The tongues 82 are convexly rounded in a semicircular shape at the end. This has a centring action for piercing on the suction tube 11 and facilitates the location of the insertion position. During the combined piercing action, the parallel longitudinal flanks of the tongues 82 are supported on the ends of the slots or insertion slots 83 or 85 and 84, respectively (compare FIG. 40).

The suction tube 11 is connected to the carrier T or the plate or the blister 105 in a fixed but movable in a staggered manner by means of a holding strap 86. The holding strap 86 is a tank-track-like body whose individual links are joined together by film hinges. The integral, materially joined composite is preferably situated centrally at the one narrow side of the plate 105 which has a rectangular outline. The fixing point of the holding strap 86 is denoted by 86' and the suction-tube end by 86". In this case, each of these is also a film hinge.

The suction tube 11, which is linked in a trapped manner suitable for disposal, can be detachably mounted on the carrier T. For this purpose, its plate 105 has a mounting 87 in the region of the other narrow side of the plate 105. This is also situated centrally. The extensions 81 or tongues 82 on the suction tube side are used for mounting at that point. They function there as linkage tongues in the form of bearing sockets 88. Axial stumps 89 on the carrier side latch into their hole or hollowed section. Said axial stumps are situated so that they provide a foldable mounting on the carrier T for the suction tube 11. The axial stumps 89, which are of nipple-like or hemispherical design, are formed on the inside of two side plates 87' of the mounting 87, which parallel side plates 87' form, together with an outer end wall 87" which joins them and the upper side of the plate 105 which optionally unloads at the rim, a bearing recess 90. The suction tube 11 can thus be folded flat on the upper side of the carrier T in a manner which protects the piercing flanks or can be transferred to a defined, projecting position ready for gripping. Reference may be made to FIGS. 41 to 43. The inside of the end wall 87" is the stop which limits the folding.

The appropriate folding control may take place by means of a housing 91 which receives the blister pack 2 plus carrier T and is closed with a lid. This is a folding case with lid. The said supply unit is fitted in this connection so that fixtures 91' of the lid which latch onto the suction tube 11 fold the suction tube 11 up into a position ready for gripping by swivelling it around the geometrical axis defined by the axial stumps 89 (FIG. 43). When set to the folded-up position, the suction tube 11 can conveniently be unlatched from the bearing recess 90 of the mounting 87 with respect to its axial stumps 89 which act as latches and similarly fitted again after use. Carrier plus blister 2 adhering to it are disposed in the lower part of the folding case and longitudinal ribs R on the base side at that point run in a matching manner between two rows of cavities. At the apex, said longitudinal ribs R have insertion openings 83' for the ends 82' of the tongues 82, which insertion openings 83' are aligned with respect to the individual slots 83 of the blister (FIG. 43b).

The joining of the suction tube 11 to the supply unit ensures a time-limited use of the latter so that a fresh suction tube 11 is therefore always used with every new unit T/2 or blister 2. Provided they are necessary for comprehension, the reference numerals of the exemplary embodiments explained at the outset are used analogously, in some cases without repetitions in the text.

Now to device V in accordance with the fourth exemplary embodiment (FIGS. 45 to 52): the extension 81, which undertakes the protection of the thrusting flanks, is now of tubular design instead of fork-shaped. Specifically it is a sleeve H mounted in a longitudinally displaceable manner on the or at the suction tube 11. Said sleeve extends over the insertion end of the suction tube 11, that is to say that end facing away from the mouthpiece opening 42. Said insertion end 92 is approximately comparable to the plunger section 27 of the first exemplary embodiment.

The insertion end 92 continues into a rear guide shaft 93. The rear guide shaft 93 is fixed on the outside radially such that it projects freely within the body forming the suction tube 11. The radial clearance is achieved by a groove 94, open in the piercing direction, of the suction tube 11. This may be an annular groove.

The extension 81 designed as a sleeve H is secured in position in its two displacement limit positions. For this purpose, the sleeve H can be latched both in the position (FIG. 47) projecting beyond the piercing flanks, that is to say cutting edge 12 and the two adjacent plunger blades 14, and in the pushed-back position (FIG. 50) exposing the piercing flanks. In the pushed-back position exposing the piercing flanks, the flanks are situated in the cavity 1. A gap in the form of a touchable access by the fingers of the operating hand or contact with the plate 105 is, however, ruled out since, when the suction tube 11 is pulled out of the piercing position, the sleeve H is automatically pulled forwards on the guide shaft 93 as a sort of annular shield. This takes place with the participation of the carrier T, as is explained below.

An external bead 95 serves as latching means on the extension side. The latter is situated on the unsupported, that is to say projecting, end of the sleeve H.

Situated at the opposite end of the sleeve H is an internal bead 96. The latter interacts with latching steps 97 and 98. The latching step 97 is one having a steep barrier flank. The latching step denoted 98, on the other hand, has a bevelled flank. Said latching step 98 can be overcome by a pulling action on the sleeve H.

The outside wall of the sleeve H is formed as a double-arm double pawl. With regard to the relevant details, reference should be made to FIG. 46. The restoring force of the material used ensures a built-in spring action for the sleeve H. The radially oriented mobility for achieving the spring action is based on longitudinally directed slotting of the sleeve H. For this purpose, pairs of slots proceed from the two sleeve ends of the essentially cylindrical sleeve wall. The slots have the reference symbols 99 and 100, respectively. They open towards the end faces of the sleeve H in opposite directions, i.e. the slot bases are directed towards one another. The slots 99 and 100 of the two slot pairs 99, 99 and 100, 100 are situated in a common extension plane, and specifically, viewed in cross section, in diametrical zones of the circular sleeve H. The sleeve length is equal to about two to three times the external diameter of the sleeve H.

It can be seen that the slot bases are spaced apart to such an extent that a circumferential bridge 101 is left between them. That results in a defined articulation point which traverses the sleeve H and whose geometrical axis is denoted by 102 in FIG. 46. The radially oriented unlatching movement of the internal bead 96 takes place around said articulation point 102.

The circumferential bridge 101 is then interrupted by longitudinal slots 103. Said longitudinal slots 103 which pass through the entire sleeve wall are situated in a plane which is transverse to the plane which extends through the geometrical axis 102. In this way, the spring capacity of the combs or backs of the double-arm pawls of the sleeve H is increased. The longitudinal slots 103 terminate on both sides at the same distance from the end faces of the sleeve H. They (103) occupy about half the length of the sleeve H.

The external bead 95 of the sleeve H interacts in a guiding manner with the suction tube passage hole 17 of the carrier T. The holes 17 disposed in the mask-type plate 105 first interact with the respective external, upper hole rim edge 17' of the carrier T. This brings about the initial positioning. A chamfered rim edge favours a constriction of this end rim of the sleeve H. Such measures which promote the forcing inwards are also achieved with regard to the sleeve H by continuing the external bead 95 into a lead-in chamfer 106 at the end rim, situated there, of the sleeve. The forcing inward of the external sleeve 95 is utilized by the lead-in chamfer 106 for the desired easy-action forcing outwards of the internal bead 105 of the sleeve H. Said internal bead is lifted in an unhooked manner out of the latching step 97 formed by an annular groove. At the same time, with appropriate axial actuation pressure, the insertion movement of the sleeve H takes place, thus bringing about the exposure of the piercing flanks. This situation is recorded in FIG. 50. As can be seen, the internal bead 96, leaving the upper barrier flank, is deflected into the space provided by the groove 94. The sleeve H travels back. Its upper end rim encounters a groove base 107 of the groove 94. This guidance outwards is only possible as a result of the pawl function, against the restoring force of the sleeve material.

In this stripped-back position of the sleeve H, the suction tube 11 is now forced completely in the direction of the blister pack 2, and specifically until the shoulders 28 of the suction tube 11 find their stop at the upper side of the plate 105. The position is then in accordance with FIG. 50. In this position, the cavity 1 is opened and the contents are accessible for sucking out. In an appropriate movement, in accordance with which the piercing flanks do not touch the base of the cavity 1, the suction tube 11 is coupled in a latching manner to the carrier T. The inner, or lower, hole rim edge 17' of the suction tube passage hole 17 is used for this purpose. This may also be a chamfer which is engaged under in a latching manner by the rim upper side of the external bead 95 which forms a latching anchor.

The relevant latching position is more firmly set than the action of the latching step 98 on the corresponding internal bead 96 of the sleeve H. This means that the two latching positions can each be entered automatically during the insertion movement and also during the retraction movement of the suction tube 11 into the hole 17 or out of the holes 17, respectively. While the suction tube 11 is already being pulled to separate it from the carrier T, the sleeve H itself is initially still retained in the carrier T by the inner latching position. Only when the internal bead 96 has entered its latching step 97 which is provided with a steep flank, is the said latching position which initially retains the sleeve H released and the lower rim of the sleeve H is pulled forward, applying itself around the sensitive flanks like a ring shield.

In the insertion fitting of the suction tube 11, the sleeve H is guided back; after opening the cavity 1 and pulling out the suction tube 11, the sleeve H is again set to the protective overhang length.

In this fourth exemplary embodiment, an additional air suction stream z is also effected. In this case, the longitudinal slots 103 and the annular space remaining on the outside of the sleeve H are used as passage cross sections, comparable with the transverse ventilating holes 43. In addition, tunnel 108, which forms a transverse opening, is left near the shoulder for the appropriate connection to the atmosphere.

All the features disclosed are essential to the invention. In the disclosure of the application, the disclosure content of the associated/attached priority documents (copy of the preliminary application) is also incorporated in its full content, also for the purpose of concomitantly including features of said documents in the claims of the present application.

What is claimed is:

1. Apparatus including a device for emptying powder-containing cavities sealed by a covering foil and a carrier carrying said cavities and having slots, said device including a suction tube which can be located by hand and which has a leading end, positioned and guided relative to the cavity, to pierces the covering foil while leaving a free cross section for air to flow into the cavity, the leading end of the suction tube having axially projecting cutting flanks and adjacent extensions which are guided in said slots in said carrier in a shape-locked/rotationally fixed manner so as to guide said cutting flanks into said cavities, in which carrier the cavities can be used as blister-packs.

2. Apparatus according to claim 1 further comprising structure guiding the suction tube with respect to the carrier which is such that the suction tube can be moved consecutively in two planes situated perpendicularly with respect to one another.

3. Apparatus according to claim 1, wherein said adjacent extensions include at least two extensions situated oppositely at a distance and projecting beyond the cutting flanks in an axial direction of the suction tube.

4. Apparatus according to claim 1 characterized in that the adjacent extensions are formed as flat tongues.

5. Apparatus according to claim 1, wherein said slots include main slots which include respective bases and single slots which proceed from the bases of the main slots.

6. Apparatus according to claim 2 characterized in that, in one of the two planes, the suction tube can be displaced and guided in a foldable and a linear manner.

7. Apparatus according to claim 1 wherein said carrier has suction tube positioning free spaces situated underneath the slots.

8. Apparatus according to claim 1, characterized in that the suction tube is continuously displaceable in said slots of the carrier, and said slots are situated on both sides of the cavities.

9. Apparatus according to claim 4 further comprising an additional swivellable fitting of the tongues to the carrier with the suction tube not yet inserted.

10. Apparatus according to claim 4 wherein said carrier has axial stumps that can mate with openings on said tongues.

11. Apparatus according to claim 4 wherein said carrier has holes aligned with respective cavities and the tongues have arc-shaped end edges that serve as guides during positioning and moving of the cutting flanks of the suction tube into the holes.

12. Apparatus according to claim 1, characterized in that the tongues are arc-shaped such that they can enter into the slots of the carrier at the same time that the suction tube lies flat above said carrier.

13. Apparatus according to claim 1, wherein the carrier has penetration channels proceeding from the slots and the tongues each have a protrusion which can be moved into a said penetration channel from the slot.

14. Apparatus according to claim 13, wherein said cutting flanks include a piercing cutting flank, and wherein said carrier has holes aligned with said cavities and the suction tube has a plunger section which can be moved into the holes and which is disposed in a set back manner with respect to the piercing cutting flank in such a way that it supplements a linear guidance of the suction tube when the protrusions enter the penetration channels.

15. Apparatus according to claim 1, wherein said carrier has holes aligned with said cavities and said suction tube has shoulders, and said carrier has regions at the side of the holes that receive said shoulders when said cutting flanks are inserted into said cavities.

16. Apparatus according to claim 1, wherein said cutting flanks include a piercing cutting flank and adjacent plunger blades, and wherein the piercing cutting flank extends below said plunger.

17. Apparatus according to claim 1, further comprising a mounting, foldable by means of a lid, for storing the suction tube.

18. Apparatus according to claim 1, wherein said carrier has a lid for covering the suction tube when it is folded away.

19. Apparatus according to claim 1, wherein the cavities and foil are included in a blister pack, and wherein the carrier includes a narrow-side end wall and a lid that secures the blister pack by means of said narrow-side end wall when the blister pack is in a pushed-in position.

20. Apparatus according to claim 1, wherein the cavities and foil are included in a blister pack, and wherein the carrier includes a lid that is pivotal and wherein the lid includes fixtures which latch on the suction tube and raise the suction tube in a swivelling manner into a position ready for gripping as the lid is pivoted open.

21. Apparatus according to claim 1, wherein the carrier includes a comb-type projecting row of teeth having tooth gaps in which the suction tube is guided during the piercing movement of the suction tube into said cavities.

22. Apparatus according to claim 21, wherein the suction tube has ribs which travel into the tooth gaps during piercing movement of the suction tube, which tooth gaps are disposed in accordance with the spacing of the blister-pack cavities.

23. Apparatus according to claim 1, characterized in that the suction tube latches in a downward insertion position.

24. Apparatus according to claim 4, wherein the tongues have an articulated arrangement, and the suction tube can be rotated around a transverse axis as a consequence of the articulated arrangement at its tongues.

25. Apparatus according to claim 4, characterized in that said suction tube has shoulders and the tongues are disposed in pairs, are of rotationally symmetrical design, and are supported in a folded-away position of the suction tube on said shoulders.

26. Apparatus according to claim 4 wherein the cavities and foil are included in a blister pack, and wherein the carrier is sheet-like and the blister pack has individual insertion slots for the tongues to enter.

27. Apparatus according to claim 26 wherein said individual insertion slots are congruent with said individual insertion slots in the carrier.

28. Apparatus according to claim 26, characterized in that the length of the individual insertion slots is equal to the width of the tongues.

29. Apparatus according to claim 1, characterized in that the carrier is of bar-type design and has a rectilinear row of suction tube passage holes on one side surface, which holes are situated congruently with the cavities.

30. Apparatus according to claim 29, characterized in that the holes are connected together by narrower open cross sections.

31. Apparatus according to claim 1 wherein said cavities are formed in a core piece of a blister-pack bar having side surfaces.

32. Apparatus according to claim 31, characterized in that the core piece of the blister-pack bar has a polygonal cross section with cavities situated on the sides thereof and can be inserted into a plurality of positions in the carrier, which positions can be rotated around a longitudinal central axis of the carrier.

33. Apparatus according to claim 32, characterized in that the blister-pack bar can be pushed into the carrier in the longitudinal direction.

34. Apparatus according to claim 32, characterized in that the blister-pack bar has a square cross section and a row of cavities on each of all the four sides.

35. Apparatus according to claim 1 wherein the cavities are provided in a folded blister-pack hollow bar which is enclosed by an insertion cage which is formed with openings corresponding to the position of the cavities.

36. Apparatus according to claim 35, characterized in that the carrier has a core bar which plunges into the internal cross section of the blister-pack hollow bar.

37. Apparatus according to claim 1, characterized in that said core bar has four flanks that are formed as supporting base for said cavities.

38. Apparatus according to claim 35, characterized in that the blister-pack hollow bar latches in the pushed-in position.

39. Apparatus according to claim 31, characterized in that the cavities of all the side surfaces are each situated on a common transverse plane of the core piece.

40. Apparatus according to claim 1, characterized in that said cavities and covering foil are provided in a blister-pack bar and the suction tube is seated in a straddling manner on the blister-pack bar.

41. Apparatus according to claim 1, characterized in that said cavities and covering foil are provided in a blister-pack bar, and the suction tube is seated in a releasable connection on the bar and, when the bar is pushed into the carrier, the connection is automatically released.

42. Apparatus according to claim 1, characterized in that said cavities and covering foil are provided in a blister-pack structure having holes, and the suction tube has flat sides having studs which enter in a friction-locked manner into said holes.

43. Apparatus according to claim 1, characterized in that said carrier has a row of teeth with lead-in lifting protrusions having chamfers.

44. Apparatus according to claim 1, wherein the cavities are provided in a folded blister-pack hollow bar which is enclosed by an insertion cage having an end face provided with use symbols.

45. Apparatus according to claim 1, wherein the cavities are provided in a folded blister-pack hollow bar which is enclosed by an insertion cage having an end wall that is provided with authenticity sealing bridges.

46. Apparatus according to claim 1, wherein said carrier has a cap-shaped lid that can be moved in the course of the folding of said suction tube into a lowered position.

47. Apparatus according to claim 46, wherein the carrier has an upper side and a lower side and the lid has an arm which projects transversely and which is guided in an articulated manner and displaceably along the upper side and, in addition, is connected by means of a connecting rod to the lower side.

48. Apparatus according to claim 47, characterized in that said lid has a longitudinal slot and the connecting rod can be displaced in said longitudinal slot of the lid.

49. Apparatus according to claim 47, further comprising a second arm which projects transversely and which is guided in an articulated manner and displaceably along the upper side and wherein each arm can be displaced with a guide stud in a guide slot of the carrier.

50. Apparatus according to claim 49, characterized in that the guide slot continues in a downwards-directed section in such a way that, when the lid is displaced, a respective lifting or lowering movement of the lid is brought about in such a way that it travels over a folded away suction tube without contact.

51. Apparatus according to claim 1, characterized in that the carrier has longitudinal ribs that each enter between two rows of said cavities.

52. Apparatus according to claim 1, wherein the cavities are provided in a blister-pack, and the carrier has, which enter into holes of the blister-pack for the purpose of retaining the blister-pack on the carrier.

53. Apparatus including a device for emptying powder-containing cavities sealed by a covering foil and a carrier carrying said cavities and having respective holes aligned with said cavities, said device including a suction tube which can be located by hand and which has a leading end, positioned and guided relative to the cavity, to pierce the covering foil while leaving a free cross section for air to flow into the cavity, the said device including cutting flanks on said leading end and a sleeve which is disposed in a longitudinally displaceable manner on the leading end of said suction tube and encloses the cutting flanks in a pushed-forward position and which positions itself at respective rims of said holes of the carrier, into which carrier the cavities can be inserted as a blister packs.

54. Apparatus according to claim 53, characterized in that the sleeve can be displaced both into a position projecting beyond the cutting flanks and into a pushed-back position which exposes the cutting flanks.

55. Apparatus according to claim 53, characterized in that two latch positions are automatically entered during the insertion movement and retraction movement of the suction tube in one of the holes.

56. Apparatus according to claim 53, characterized in that said sleeve has interaction with the rim of the hole in the carrier.

57. Apparatus according to claim 56, characterized in that the sleeve has an external bead which interacts with the hole rim edge of the carrier at the unsupported end and has, at the opposite end, an internal bead which interacts with latching steps of the suction tube.

58. Apparatus according to claim 53, characterized in that the sleeve is of a radially resilient design as a consequence of longitudinally directed slotting.

59. Apparatus according to claim 53, characterized in that said sleeve has two slot pairs proceeding from the sleeve ends that are directed towards one another up to a central circumferential bridge of the sleeve.

60. Apparatus according to claim 59, characterized in that the circumferential bridge is interrupted by longitudinal slots situated in a circumferentially offset manner in the sleeve wall.

61. Apparatus according to claim 57, characterized in that the external bead forms a lead-in chamfer for push-in movement of said sleeve.

62. Apparatus according to claim 61, characterized in that the forcing-inwards of the external bead by the lead-in chamfer contributes to a forcing-outwards of the internal bead of the sleeve.

63. Apparatus according to claim 61, characterized in that the external bead is latched in an overcomable manner with regard to its pushing-in movement in the insertion limit position.

64. Apparatus according to claim 60, characterized in that the longitudinal slots which interrupt the circumferential bridge provide additional air suction flow.

65. Apparatus according to claim 53, characterized in that said suction tube has entry bores for additional air suction flow that are situated to generate an eddy when the additional air enters a main channel of the suction tube.

* * * * *